United States Patent
De La Zerda et al.

(10) Patent No.: US 10,716,867 B2
(45) Date of Patent: Jul. 21, 2020

(54) HIGH-RESOLUTION OPTICAL MOLECULAR IMAGING SYSTEMS, COMPOSITIONS, AND METHODS

(71) Applicant: The Board of Trustees of the Leland Stanford Junior University, Stanford, CA (US)

(72) Inventors: Adam De La Zerda, Palo Alto, CA (US); Orly Liba, Stanford, CA (US); Elliott Sorelle, Stanford, CA (US); Bryan Knysh, Saratoga, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 12 days.

(21) Appl. No.: 15/548,151

(22) PCT Filed: Feb. 5, 2016

(86) PCT No.: PCT/US2016/016745
§ 371 (c)(1),
(2) Date: Aug. 2, 2017

(87) PCT Pub. No.: WO2016/127039
PCT Pub. Date: Aug. 11, 2016

(65) Prior Publication Data
US 2018/0264144 A1   Sep. 20, 2018

Related U.S. Application Data

(60) Provisional application No. 62/113,220, filed on Feb. 6, 2015.

(51) Int. Cl.
*A61K 49/00* (2006.01)
*A61B 5/00* (2006.01)
*A61K 49/04* (2006.01)
*C01G 7/00* (2006.01)
*C08L 25/06* (2006.01)
*B82Y 5/00* (2011.01)

(52) U.S. Cl.
CPC ........ *A61K 49/0093* (2013.01); *A61B 5/0066* (2013.01); *A61B 5/0084* (2013.01); *A61K 49/0056* (2013.01); *A61K 49/0065* (2013.01); *A61K 49/0428* (2013.01); *C01G 7/00* (2013.01); *C08L 25/06* (2013.01); *A61K 2123/00* (2013.01); *B82Y 5/00* (2013.01); *C01P 2004/04* (2013.01); *C01P 2004/16* (2013.01); *C01P 2004/64* (2013.01); *C08L 2203/02* (2013.01)

(58) Field of Classification Search
CPC ............ A61K 49/0093; A61K 49/0056; A61K 49/0428; A61K 49/0065; A61K 2123/00; A61B 5/0084; A61B 5/0066; C01G 7/00; C08L 25/06; B82Y 5/00; C01P 2004/04; C01P 2004/16; C01P 2004/64
See application file for complete search history.

(56) References Cited

U.S. PATENT DOCUMENTS

| | | |
|---|---|---|
| 4,035,068 A | 7/1977 | Rawson |
| 5,440,664 A | 8/1995 | Harrington et al. |
| 6,466,368 B1 | 10/2002 | Piepel et al. |
| 8,551,727 B2 | 10/2013 | Kwon et al. |
| 9,445,749 B2 | 9/2016 | Erickson et al. |
| 9,686,395 B2 | 6/2017 | Erickson et al. |
| 2003/0151742 A1 | 8/2003 | Silvermintz et al. |
| 2007/0012777 A1 | 1/2007 | Tsikos et al. |
| 2007/0155021 A1* | 7/2007 | Zhang .................... B82Y 30/00 436/518 |
| 2008/0007733 A1 | 1/2008 | Marks et al. |
| 2009/0040527 A1 | 2/2009 | Popescu et al. |
| 2009/0284713 A1 | 11/2009 | Silverstein et al. |
| 2010/0057068 A1 | 3/2010 | Lee |
| 2010/0266508 A1 | 10/2010 | Kattumuri et al. |
| 2010/0327175 A1 | 12/2010 | Nesterets et al. |
| 2011/0110858 A1 | 5/2011 | Aras et al. |
| 2011/0134436 A1 | 6/2011 | Podoleanu et al. |
| 2011/0242487 A1 | 10/2011 | Yuasa et al. |
| 2013/0044185 A1 | 2/2013 | Krishnaswamy et al. |
| 2013/0088723 A1 | 4/2013 | Feldkhun |
| 2013/0314716 A1 | 11/2013 | Tearney et al. |
| 2013/0329226 A1 | 12/2013 | Matsubara et al. |
| 2014/0218744 A1 | 8/2014 | De Boer et al. |
| 2015/0168126 A1 | 6/2015 | Nevet et al. |
| 2018/0223260 A1* | 8/2018 | Aprikyan ............. C12N 5/0696 |
| 2018/0299251 A1 | 10/2018 | Liba et al. |

OTHER PUBLICATIONS

Perez-Juste et al., Adv. Funct. Mater. 2004, 14, No. 6 Jun.*
Jana et al., J. Phys. Chem. B 2001, 105, 4065-4067.*
International Search Report for PCT Application No. PCT/US16/16745, dated Jul. 26, 2016.
Alexandridis, P. "Gold Nanoparticle Synthesis, Morphology Control, and Stabilization Facilitated by Functional Polymers," Chem. Eng. Technol, 34, No. 1, 15-28 (2011).
Dousset, V. et al., "MR Imaging of Relapsing Multiple Sclerosis Patients Using Ultra-Small-Particle Iron Oxide and Compared with Gadolinium," American Journal of Neuroradiology 27: 1000-05 (May 2006).
Halbreich, A. et al., "Biomedical applications of maghemite ferrofluid," Biochimie 80, 379-90 (1998).
Kang, Y. et al., "Core/Shell Gold Nanoparticles by Self-Assembly and Crosslinking of Micellar, Block-Copolymer Shells," Angew. Chem. Int. Ed. 44, 409-412 (2005).

(Continued)

*Primary Examiner* — Robert S Cabral

(57) ABSTRACT

A composition includes a plurality of gold nanoparticles each having at least one surface. The gold nanoparticles have an average length of at least about 90 nm and an average width of at least about 25 nm.

23 Claims, 19 Drawing Sheets

(56) References Cited

OTHER PUBLICATIONS

Kleinschnitz, C. et al., "In vivo detection of developing vessel occlusion in photothrombotic ischemic brain lesions in the rat by iron particle enhanced MRI," Journal of Cerebral Blood Flow and Metabolism 25. 1548-1555 (2005).

Li, L. et al., "Synthesis, Properties, and Environmental Applications of Nanoscale Iron-Based Materials: A Review," Environ. Sci. Technol. 36, 405-431 (2006).

McDonald, M. et al., "Investigations into the Physicochemical Properties of Dextran Small Particulate Gadolinium Oxide Nanoparticles," Academic Radiology 13(4):421-427 (Apr. 2006).

Okitsu, K. et al., "Sonolytic Control of Rate of Gold (III) Reduction and Size of Formed Gold Nanoparticles: Relation between Reduction Rates and Sizes of Formed Nanoparticles," Bulletin Chemical Society Japan 75(10):2289-96 (2002).

Okitsu, K. et al., "Sonochemical Synthesis of Gold Nanoparticles: Effects of Ultrasound Frequency," Journal of Physical Chemistry, 109(44):20673-20675 (2005).

Tomar, A. et al., "Short Review on Application of Gold Nanoparticles," Global Journal of Pharmacology 7 (1):34-38 (2013).

Valois, C. et al., "The effect of DMSA-functionalized magnetic nanoparticles on transendothelial migration of monocytes in the murine lung via a B2 integrin-dependent Pathway," Biomaterials 31(2):366-374 (2010).

Vinodgopal, K. et al., "Sonolytic Design of Graphene—Au Nanocomposites. Simultaneous and Sequential Reduction of Graphene Oxide and Au (III)," Journal of Physical Chemistry Letters 1(13):1987-93 (2010).

International Search Report and Written Opinion for PCT Application No. PCT/US16/57656, dated Jan. 17, 2017.

\* cited by examiner

HIGH-RESOLUTION OPTICAL MOLECULAR IMAGING SYSTEMS, COMPOSITIONS, AND METHODS

This application is a U.S. national stage filing under 35 U.S.C. § 371 of International Application No. PCT/US2016/016745, entitled "HIGH-RESOLUTION OPTICAL MOLECULAR IMAGING SYSTEMS, COMPOSITIONS, AND METHODS," filed Feb. 5, 2016, which claims priority to U.S. Provisional Application No. 62/113,220 titled "HIGH-RESOLUTION OPTICAL MOLECULAR IMAGING SYSTEMS, COMPOSITIONS, AND METHODS," filed Feb. 6, 2015, the entire disclosure of each of which is incorporated herein by reference in its entirety.

STATEMENT OF GOVERNMENT SUPPORT

This invention was made with government support under grant no. FA9550-15-1-0007 awarded by the United States Air Force, and grant no. NIH DP50D012179 awarded by the National Institute of Health. The government has certain rights in the invention.

BACKGROUND

Existing clinical imaging systems (e.g., X-Ray, ultrasound, MRI, PET) used for cancer detection and diagnostics are designed to provide relatively low-resolution images of large body areas such as the breast, lungs, brain, and other similar organs and tissue. They are intended to detect potentially abnormal looking tissue structure that might represent the existence of cancer in the body. Interpreting these images to decide if an abnormality might be cancer, and therefore subjecting the patient to more testing, requires a highly skilled radiologist. Even then, this results in many false positive and some false negative interpretations due to poor spatial resolution, poor contrast, and complexity in visually assessing the image. Confirming that any abnormal looking structure in an image is in fact cancer involves performing a biopsy, removing a sample of the tissue from the body and observing it under a microscope. While cumbersome for detecting cancer, these techniques are completely impractical for cancer imaging applications such as identifying drug resistance and treatment monitoring. For these applications, current imaging systems are unable to detect detailed cellular signaling and biological processes within the tumor, and multiple biopsies through the treatment would be too invasive.

There is hence a need for molecular imaging systems, compositions, and methods capable of detecting and characterizing individual cells and biological processes within the body in a fast, minimally invasive procedure.

DETAILED DESCRIPTION

The optical molecular imaging systems, compositions and methods described herein represents over 1000-fold improvement in spatial resolution from conventional molecular imaging systems (e.g., X-Ray, ultrasound, MRI, PET), while still maintaining a clinically significant depth of imaging penetration (FIG. 1). Numerous new applications for molecular imaging in the study of medical and biological processes in healthy and diseased tissue in living subjects are enabled by these systems and methods. Applications such as, but not limited to, detecting and measuring intra-tumor heterogeneity, measuring tumor drug response, and tumor surgical margin detection can potentially save the lives of many people inflicted with cancer. Other diseases (e.g., autoimmune disorders) may also benefit from real-time, in vivo, monitoring of intercellular signaling of abnormal cellular processes and their response to treatment.

Systems, compositions, and methods described herein can also have a significant impact on the scientific study of biology, such as cancer mechanisms for growth and metastasis. Currently, cancer researchers study in vivo cancer biology by viewing tumor cells as a "black-box," inferring cellular processes such as signaling and apoptosis based on externally viewable phenomenon. Systems and methods described herein can allow study of live signaling and other processes associated with cancer growth and metastasis, to better understand how they work, and devise better solutions to target and kill cancer cells. Further, filling the technology gap by allowing imaging at a single cell resolution and multi millimeter depth of penetration may lead to other potential applications in basic biology, such as visualizing cell-cell interactions during health and disease states.

Figures 1A, 1B, 1C, 1D, 1E, 1F:
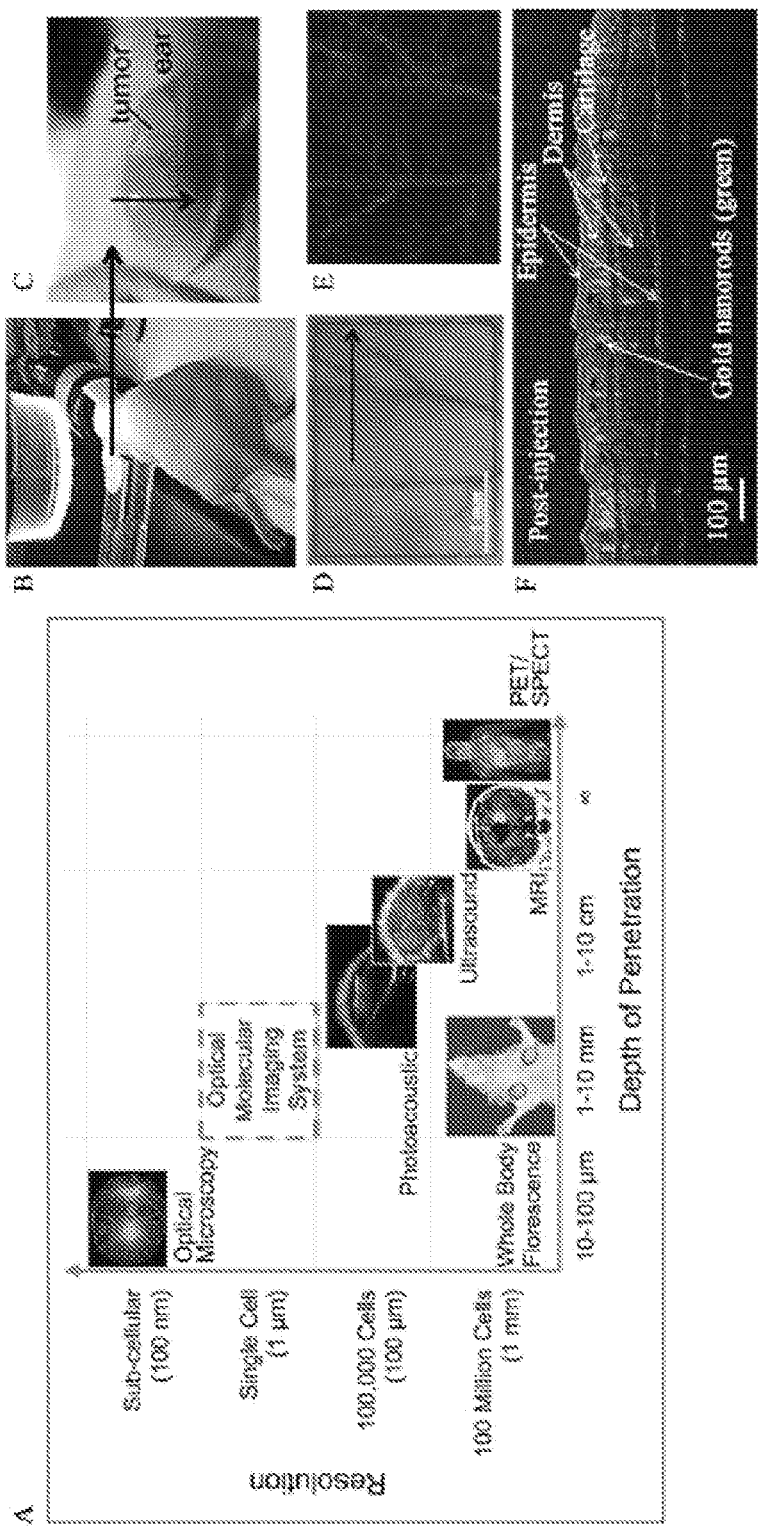
FIG. 1. A) Graph showing imaging void and targeted application. B) System imaging of a mouse ear following intravenous injection of gold nanorods (GNRs). C) The regions scanned in 2D (black arrow) and 3D (red frame). D) Tumor vasculature imaged in 3D (2D projection image is shown in gray). Notice the large (healthy) blood vessel and the many small and tortuous blood vessels that extend from it into the tumor. E) The result of the angiography algorithm of the 3D scan shown by the red frame in D. F) Ear cross-section showing MOZART image of GNRs (green signal) with ultra-high spatial resolution (~4 μm) and sensitivity, as few as 5 GNRs were sufficient to create a distinguishable signal. G) A three dimensional visualization of the mouse ear showing the raw OCT signal in gray scale and the GNRs spectral signal in the blood vessels in color.
Figure 2:
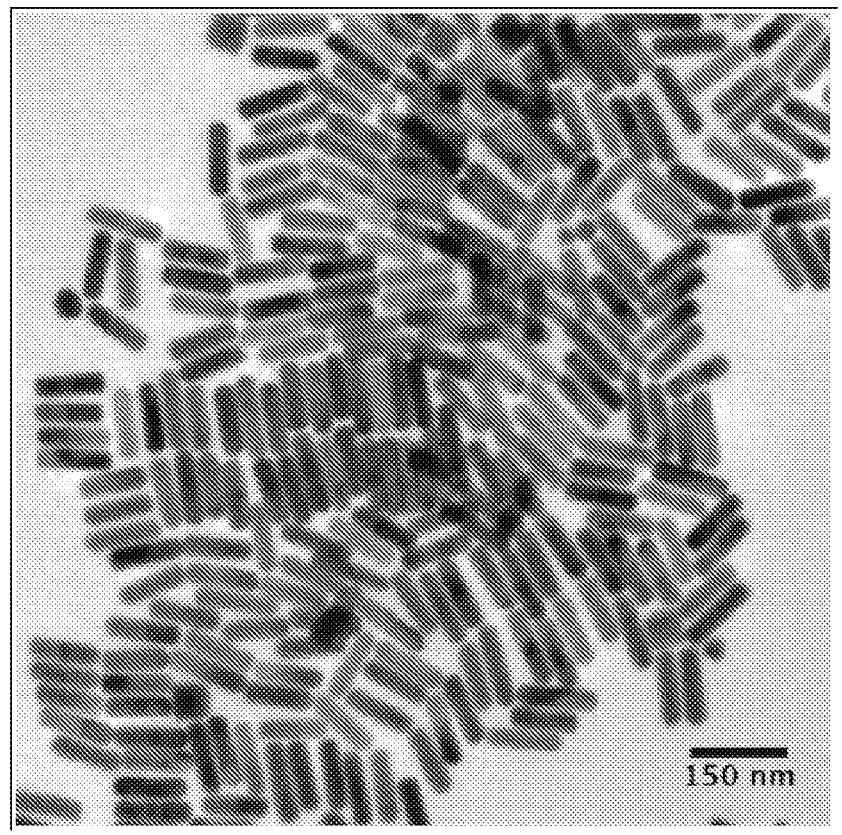
FIG. 2. Transmission electron microscope image of gold nanorods (GNRs)
Figure 3:
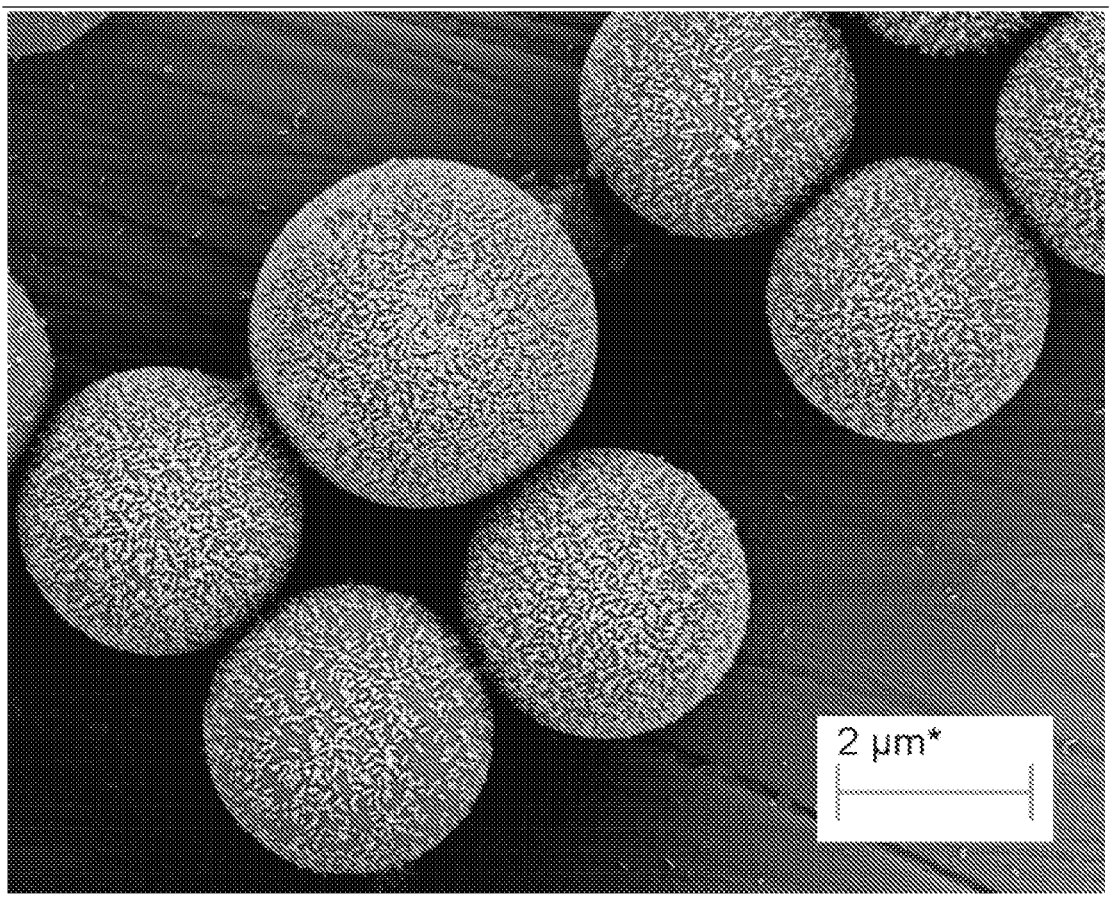
FIG. 3. Transmission electron microscope image of GNR covered microbeads.
Figure 4:
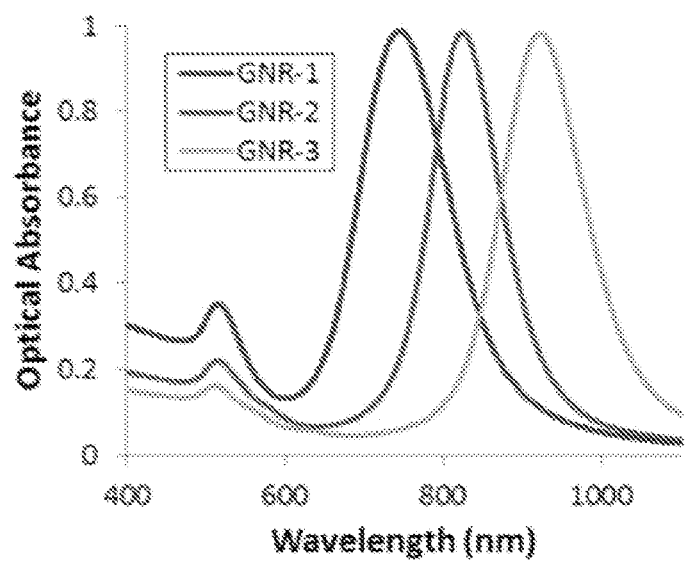
FIG. 4. Optical absorbance of 3 GNRs with different aspect ratio resulting in 3 different spectra. Gold nanorods (GNRs) can be synthesized to have a tunable peak wavelength.
Figure 5:
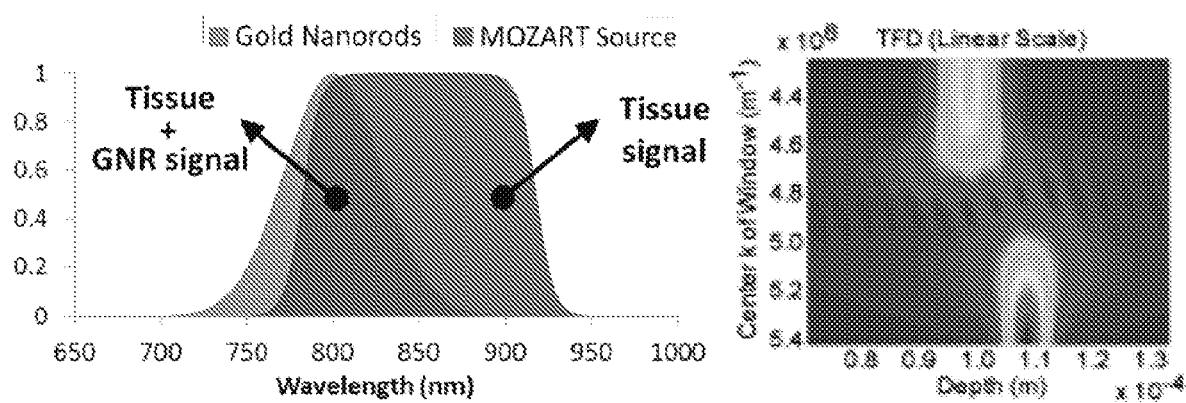
FIG. 5. A. Optical spectra of the light source and the GNRs. B. Simulation of spectral unmixing algorithm of two spectrally different scattering objects 100 μm from each other.

In some embodiments, systems, compositions, and methods described herein can provides a spatial resolution of less than 2 µm—smaller than the size of a single cell, over a tissue depth of up to 2-3 mm (FIG. 1F). The system measures the diffraction spectrum of a coherent light beam off of a scattering nanoparticle, such as a rod-shaped gold nanoparticle (also interchangeable referred to as a "gold nanorod", or GNR) (FIG. 2) or GNR-covered microbeads (FIG. 3). The GNRs are non-toxic and can be functionalized with antibodies capable of binding to cancer biomarkers for characterization of cell expression or other cellular signaling markers for identifying active cellular processes. Functionalized gold nanoparticles can be used as imaging agents targeted to specific biomarkers in a tumor. Systems, compositions, and methods described herein can image the presence of GNRs in live tissues with ultrahigh sensitivity and spatial resolution in real-time. By changing the physical dimensions of the GNRs, GNRs with different peak wavelengths can be created, allowing for imaging of several biomarkers in a tumor substantially simultaneously (FIGS. 4 and 5). GNRs may also be functionalized to image biomarkers such as interleukins and/or other cytokines associated with autoimmune disorders and inflammatory diseases. Visualizing the signaling cascade in vivo and in real time can lead to a better understanding of disease progression and the development of more effective targeted therapeutics.

Figure 1G:
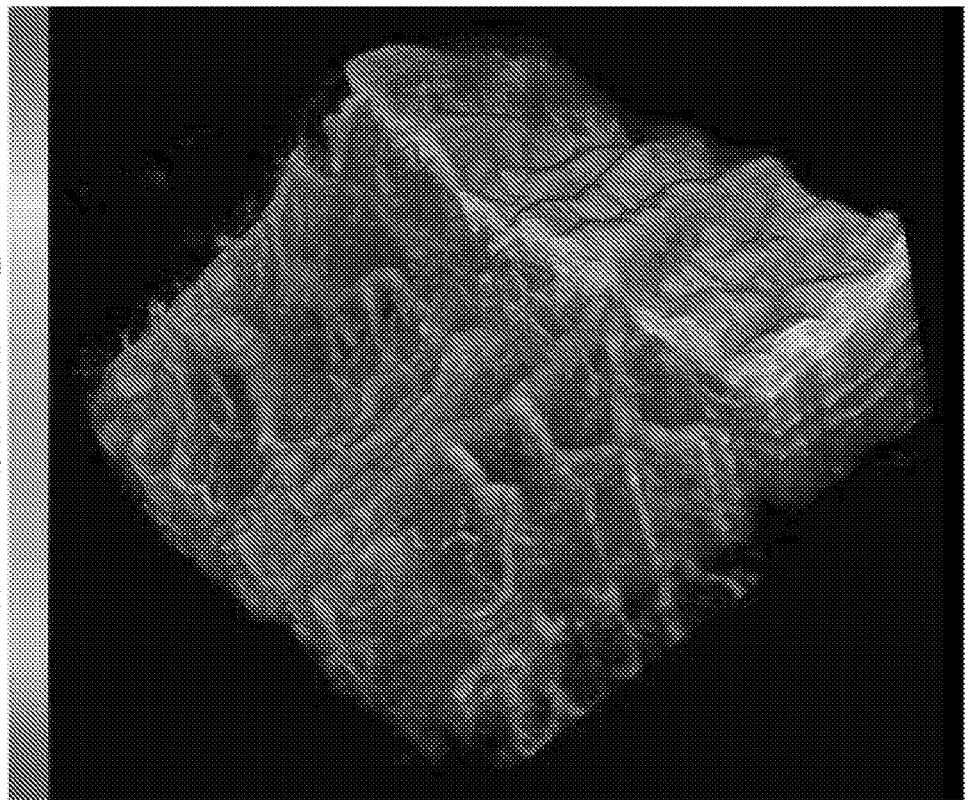

In some embodiments, typical optical coherence tomography (OCT) instrumentation can be employed to acquire data from live tissues that were previously administered with contrast agents such as functionalized GNRs, and/or to process the data with signal processing methods and/or to perform imaging processing to result in a high quality image that represent the three-dimensional distribution of the imaging agents in the tissue. FIG. 1G illustrates a 3D image that shows a raw OCT signal in gray scale and the GNRs spectral signal in color (colored portion of the image I included above). The 3 images are inherently co-registered, allowing visualization of the molecular heterogeneity of the tissue in the context of tissue structure and anatomy, and how far each cell is from a blood vessel or lymph vessel.

In some embodiments, aspects of the systems, compositions, and methods described herein can include methods that enables the detection of nanoparticles in tissue based on their unique scattering spectrum. In these methods, nanoparticles with a non-uniform scattering spectrum can be detected by looking at the scattering spectrum. In some embodiments, approaches disclosed herein can analyze the differences in scattering intensity between two separated spectral bands. In some embodiments, the approaches disclosed herein can include at least some of the following non-limiting steps:

a) Raw interference spectrum as detected by a spectrophotometer, such as a spectrophotometer of a Spectral Domain Optical Coherence Tomography (SDOCT) system, is received b) Dispersion compensation (described in greater detail below)
c) Normalization by the source spectrum
d) Separation of the spectrum into at least two bands
e) Construction of the spatial images of the two bands
f) If there is a spectrally uniform object in the image, a balancing stage is performed to compensate for residual imbalances between the bands.
g) Subtracting the spatial images to see the difference between them, such as in a difference image.

The result can be displayed in various ways, such as, for example, the total scattering intensity, the spectral difference image, and/or the like, and combinations thereof. In some embodiments, a speckle variance image indicating flow can be combined with the results in any suitable manner. Since regions that have flow do not suffer from speckle noise, looking at the spectral difference image at the regions in which there is flow can provide an overall more reliable and less noisy image.

Dispersion can be broadly described as a property of material, in which different wavelengths accumulate different phases and subsequently, effectively, travel different distances.

Dispersion can manifests in the OCT image as a blurring of vertical edges. In the spectral image, dispersion can cause a shift between the bands. Subtracting the bands to create the spectral image can cause severe artifacts. In some embodiments, dispersion compensation can be accomplished by using the spectral image as a measurement for the dispersion and minimizing the artifact caused by the shift between the bands. In some embodiments, dispersion compensation includes iteratively modifying the quadratic phase coefficient of the spectrum until the artifact is minimized. The artifact can be measured by the total absolute signal of the spectral (diff) image.

In some embodiments, the spectral image can be improved by compensating for intrinsic imbalances between the bands. Such imbalances could be caused, for example, by chromatic aberrations in the OCT lens or by the wavelength dependent sampling rate, or by the roll off effect which can be caused by the sampling of the spectrum, and/or the like. In some embodiments, these imbalances can be compensated for on a per image basis when there is a sample in the image which is wavelength independent (in the range of the light source). A region in the uniform sample is selected manually or automatically. In some embodiments, blood vessels can be automatically removed from this region for instances in which the vessels contain a high concentration of the gold nanoparticles. Next, the average signal in both of the bands is calculated as a function of depth. The signal as a function of depth is fitted to a polynomial (of degree 5-7) in order to smooth it. The gain needed to compensate for the spectral imbalances is the ratio between the polynomial of each band and their average. Each band is divided by the gain before subtracting the bands to create the spectral image.

Aspects of the systems, compositions, and methods disclosed herein are also directed to processes for functionalization and molecular targeting of large (e.g., in the size range of about ~130 nm×30 nm) Gold Nanorods (GNRs), and composition including the functionalized GNRs. GNRs are desirable contrast agents for spectral imaging because they can be made to have finely tuned spectral absorbance peaks in the near infrared regime of the electromagnetic spectrum.

Functionalization of GNRs: The process for functionalizing and targeting large GNRs can be generally described as follows. First, GNRs synthesized by the protocol described in Murray et al 2013 (incorporated herein by reference) are washed 1× by centrifugation to remove excess CTAB from the GNR growth solution. The pelleted GNRs are then resuspended in distilled deionized water to a concentration of ~1 nM. Then, 1 mM polystyrene sulfonate (PSS, MW~70,000 Da) is added in a 1:10 ratio to the 1 nM GNRs (for example, 100 μL of PSS per 1 mL GNRs). PSS is a high molecular weight anionic polymer that electrostatically adsorbs to the surface of the GNRs, providing stabilization to the colloidal suspension of nanoparticles. In some embodiments, other anionic polymers, such as polyacrylic acid (PAA), can be used instead of PSS. The GNR-PSS mixture is immediately mixed by vortexing and left to react at room temperature for 5 minutes. Afterward, the PSS-coated GNRs are pelleted by centrifugation, the supernatant is removed, and fresh distilled deionized water is added to the PSS-GNR pellet. The process of adding PSS in a 1:10 ratio to the GNRs and washing is repeated twice to ensure complete surface stabilization of the particles. Once GNRs have been coated in PSS, they are mixed with one of several thiolated PEG reagents (at 1 mg PEG reagent per 1 mL of 1 nM PSS-GNRs) for a minimum of 6 hours at about 25° C. Untargeted control PSS-GNRs (those without molecular specificity for a given cell surface receptor or other biological marker) are reacted with methoxy-terminated PEG reagents (mPEG) such as $mPEG_{5000}$-SH (MW~5000 Da). Targeted PSS-GNRs are instead incubated with Biotin-$PEG_{5000}$-SH (also at 1 mg PEG per 1 mL of 1 nM PSS-GNRs). In the case of both targeted and untargeted GNRs, the thiol (SH) group of the PEG reagent binds to the PSS-GNR surface while the other end of the PEG molecule (methoxy or biotin group) remains unreacted. After the 6-hour incubation, the particles are washed twice by centrifugation and resuspension with distilled deionized water. After two washes, the untargeted control particles are concentrated to about 20 nM and stored at 4° C. until use. After two washes, the Biotin-PEG-PSS-GNRs are concentrated to ~10 nM and transferred to a 10 mL glass scintillation vial. Then, 100 μL of 1 mg/mL NeutrAvidin is added to the Biotin-PEG-PSS-GNRs, vortexed, and reacted at room temperature for 1 hour. During this reaction, NeutrAvidin binds with high affinity to the terminal biotin groups that are conjugated to the PSS-GNRs via the PEG linker. After 1 hour, the particles (still in the scintillation vial) are centrifuged and washed twice to remove excess/unreacted NeutrAvidin. At this point the GNRs are surface conjugated with NeutrAvidin, and any biotinylated ligand (antibody, peptide, etc.) can be added to the NeutrAvidin-GNRs to convey targeting to the desired molecular target. For example, a biotinylated version of a cyclic RGD peptide (1 mg/mL) can be added to these NeutrAvidin GNRs at a volumetric ratio of 1:500 to a solution of about 20 nM NeutrAvidin-GNRs to produce RGD-GNRs that bind specific integrin receptors including the $\alpha_v\beta_3$ that is highly expressed on certain cancer cells and angiogenic blood vessels.

In some embodiments, GNRs can be combined with polystyrene microbeads to create a contrast agent that exhibits stronger signal intensity in OCT than either agent alone. Moreover, such Bead-GNR conjugates retain some of the spectral properties of GNRs and can be clearly distinguished using OCT spectral analysis methods described herein. GNRs are desirable OCT contrast agents due to their large scattering cross-section and narrow spectral properties. Polystyrene beads also exhibit strong scattering intensity in OCT imaging. The scattering from beads is due to their large size (2-6 μm diameter) relative to the wavelengths of light used for imaging and the refractive index mismatch between polystyrene (n≈1.5) and surrounding biological media (mostly water, n≈1.33).

Synthesis of Bead-GNR Conjugates:

Bead-GNR conjugates are prepared by first functionalizing a solution of GNRs as described in the previous section on Biofunctionalization. Any stock solution of as-prepared GNRs is reacted with polystyrene sulfonate (PSS) and washed by centrifugation. PSS-GNRs are then incubated with Biotin-PEG-SH (1 mg PEG reagent per 1 mL 1 nM GNRs) for at least six hours at room temperature and subsequently washed. Biotin-GNRs can then be added to a stock of streptavidin-coated polystyrene beads in any desired ratio. The ratio of GNRs and beads depends on the surface area per bead—smaller beads have less surface area and require fewer GNRs per bead to achieve maximal surface conjugation. For example, a typical reaction ratio is 100 μL of 10 nM GNRs+10 μL of 0.1 nM beads (3 μM diameter), which is a ratio of 1000 GNRs per bead. This ratio of GNRs per bead is in excess of the theoretical maximum number of GNRs that can bind to a single bead surface based upon surface area, and it is used to ensure maximal conjugation. In general, a greater extent of bead-GNR conjugation leads to stronger scattering intensity per particle in OCT. The mixture of Biotin-GNRs and streptavidin-coated polystyrene beads is incubated at room temperature with vortexing for at least one hour. Afterwards, the sample is washed by centrifugation extensively to remove any unconjugated GNRs that remain free in solution. Centrifugation should be performed at ~1000×g for 30 seconds to 1 minute, depending on the bead size. Under these conditions, the large bead-GNR conjugates pellet while unconjugated GNRs remain free in the supernatant. The supernatant can then be removed and the pellet can be resuspended in fresh distilled deionized water. Note that these bead-GNRs are not yet targeted to a biological molecule of interest. Such targeting is achieved by further incubating the purified Bead-GNRs with excess NeutrAvidin. The NeutrAvidin binds any free Biotin moieties on GNRs bound to the bead surface. After washing away free NeutrAvidin, the particles can be incubated with any biotinylated ligand or antibody to confer molecular targeting (note that these steps are analogous to the final two steps of targeting free GNRs).

In broadest terms, systems, compositions, and methods disclosed herein allow for real-time visualization of molecular biomarkers associated with intercellular signaling and communication, in healthy and diseased states, in living subjects. This has applications in clinical diagnostics as well as basic science. Details of selected, non-limiting applications follow.

Breast Cancer Optical Biopsy and Detection of Intra-Tumor Heterogeneity—

Intratumor heterogeneity (multiple cancer cell subtypes in a single tumor) is a primary cause for an incomplete treatment response and eventual breast cancer recurrence. Breast cancer subtypes can be classified based on gene-expression profiling, which primarily corresponds to Human Epidermal Growth Factor Receptor 2 (HER2), Estrogen Receptor (ER) and Progesterone Receptor (PR) markers. The expression, or lack of expression, of these markers within a breast tumor is a critical factor in choosing the right drug, or drug combination, for a patient. Targeted drugs against these markers show significantly better outcomes over non-targeted chemotherapy. Simply measuring genetic markers at the tumor level, as it is done today, is a dramatic oversimplification of the complex cellular composition of a breast cancer tumor. Not only does intra-tumor heterogeneity result in a poor response to targeted therapies, but many patients experience a change in tumor markers as a result of the therapy. Minimally invasive molecular imaging of a breast tumor for HER2, ER and PR expression at the individual cell level using the systems, compositions, and/or method described herein can fully characterize intratumor heterogeneity. Such capability can help clinicians optimize the treatment, taking in account all cancer cell types in a breast tumor, and guaranteeing that 'no cancer cell is left behind'.

Breast Cancer Drug-Resistance Detection and Image-Guided Adaptive Drug Treatment—

The majority of breast cancer patients either have tumor cells that are innately drug resistant to their breast cancer therapy, or acquire drug-resistance during their treatment regimen. Assessing a patient's response to treatment, as done today through MRI or other techniques, by measuring gross changes in tumor volume doesn't accurately identify drug-resistance since some aggressive tumor cells continue to grow while bulk tumor cells die giving the impression of tumor shrinkage. It may take months to observe a meaningful change in tumor size, and if the treatment is not working, the doctor and patient have lost valuable time that could mean the difference between a positive or negative overall survival.

Figure 6:
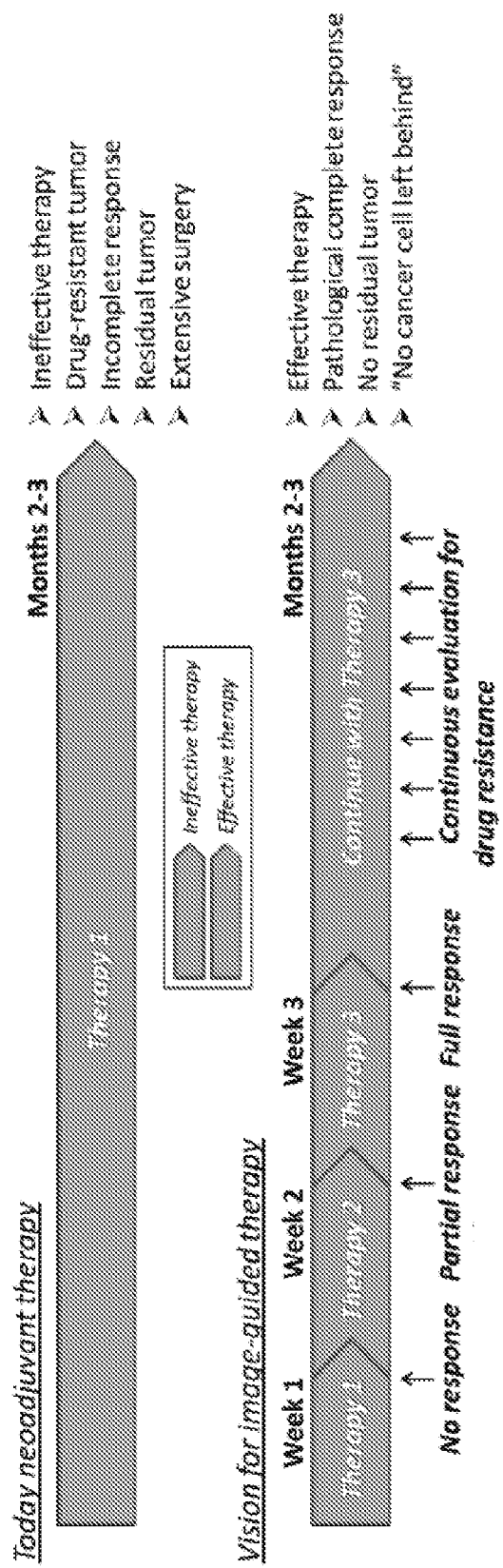
FIG. 6. Potential application in image-guided breast cancer therapy optimization and detecting drug resistance. Early detection of drug-resistance using molecular imaging allows for adjustment of neoadjuvant therapy to achieve a pathological complete response and a significantly better overall survival. In the example above, the patient had an innate resistance to the first therapy. This is discovered by 1 week later and allows the clinician to adjust the therapy repeatedly until the optimal therapy is found. The tumor is continually monitored for acquired drug-resistance, ensuring a pathological complete response.

Molecular changes in tumor cells responding to a drug occur within hours to days. Synthesis of GNRs to detect the presence of CD47, along with GNRs to detect the presence of phosphatidyl serine (PS), an indicator of cell death, allows for imaging and real-time assessment of tumor cell response to drug therapy. Thus, clinicians can visualize every single cell in a breast tumor and measure its response to therapy. Once therapy is administered, weekly imaging sessions can assess tumor response identifying innate or acquired drug-resistance as early as possible, allowing a clinician to substitute a more effective therapy (FIG. 6). This can have a significant impact on patient care, leading to patient treatment optimization targeting all breast cancer cells. This results in truly enabling personalized medicine at the molecular level, maximizing a patient's likelihood for pathological complete response, and minimizing the risk of future recurrence and metastasis.

Skin Cancer Tumor Margin Detection for Moh's Surgery—

Melanoma is the most aggressive type of skin cancer and has very high rates of mortality. An early stage melanoma can be surgically removed with a very high survival rate. Mohs surgery is a microscopically-controlled surgery used to treat melanoma. During Mohs surgery, physicians remove successive layers of skin until tumor-free margins are obtained, examining each section microscopically while patients wait in the office for several hours. Integration of optical molecular imaging into the Mohs surgery procedure would provide real-time assessment of skin cells allowing for surgeons to achieve a tumor-free margin without patients waiting extensively while successive layers of skin are fixed, stained, and examined under a microscope looking for any remaining tumor cells.

Brain Cancer Surgical Margin Detection—

Glioblastoma is the most common and deadliest primary brain tumor in adults. Surgery is an essential component in treating brain tumors, with maximal resection improving overall survival. However, glioblastoma cells are highly invasive, with finger-like protrusions infiltrating normal brain tissue making it difficult to assess surgical margins. Thus, maximal resection must be balanced with increased morbidity due to removal of normal brain tissue. Unfortunately, this leaves a residual pool of invasive cells that often results in a recurrent tumor, with virtually all glioblastoma patients experiencing disease progression within 7 to 10 months after treatment.

Systems, compositions, and methods disclosed herein can provide for in vivo cellular-level imaging of brain tumors for surgical margin detection with the ability to distinguish between cancer cells and normal tissue. In some embodiments, use of the systems, compositions, and methods described herein along with or including a robotic surgical instrument can further enhance brain cancer surgery through cellular-level, image-guided control of a robotic arm. Use in conjunction with emerging automated surgical robotic techniques will allow for maximal extent of resection while minimizing damage to normal brain tissue during brain tumor resection.

Real-Time Imaging of Intercellular Signaling Processing in Living Subjects—

Cells in the body are in constant communication with one another, sending and receiving proteins and other biomolecules back and forth. These communications ultimately determine the fate of a tissue and regulate nearly all aspects of life including health and disease. Systems, compositions, and methods described herein can monitor the biochemical communications among millions of cells in vivo at a cellular resolution in real time such as, for example, interaction between millions of cells in live mice with a minute resolution over several days.

Systems, compositions, and methods described herein can enable scientific discovery in all aspects of life sciences. It can allow for observing cells triggering other cells, as occurs in activation of a latent bacterial infection or when cancer cells in a tumor send growth signals to neighboring cells signaling them to replicate. Tumors are extremely heterogeneous and are composed of many sub-types of cancer cells, endothelial cells, and various immune cells. The communication between all these cells encodes the most fundamental activities of a tumor, including its early development, metastasis, angiogenesis, response to therapy, acquired drug-resistance and more.

Real-Time, In Vivo Imaging of the Inflammatory Response Associated with Asthma

Asthma is a heterogeneous condition with diverse causes and intrinsic development in patients. This heterogeneity manifests itself in terms of clinical features, sources of inflammation, and response to common therapies, with 25-35% of people with asthma failing to respond to inhaled corticosteroids. Each distinct asthma phenotype may be associated with a specific molecular signaling pathway, which is why targeting a single pathway can be ineffective in patients. These diverse asthma phenotypes and mechanisms leading to asthma symptoms make it a difficult condition to classify, treat, and manage therapeutically. Without effective treatment, persistent asthma can result in airway structural changes and remodeling that further complicates the condition leading to irreversible loss of lung function. Using systems, compositions, and methods disclosed to image biomarkers such as interleukin-13 (IL-13), an indicator of inflammatory asthma, and epidermal growth factor receptor (EGFR), which is correlated with epithelial remodeling and disease severity in inflammatory asthma, can help identify specific pathways underlying clinical phenotypes leading to more accurate diagnosis; identification of potential drug targets; and, predicting treatment response in the patients.

Traditional OCT systems are based on detecting coherent light scattering provided inherently by the biological tissue. While this technique works fine for imaging anatomical structure, it does not provide any molecular information on biomarker expression for cell characterization or protein expression involved in intercellular signaling, as can be obtained using the systems, compositions, and methods disclosed herein.

Over time, the development of higher resolution optics or new nanoparticles with higher optical scattering properties could potentially improve the imaging characteristics of the molecular imaging system. In addition, the discovery of new cancer and other disease biomarkers, and development of new nanoparticles functionally targeting these biomarkers, could dramatically expand the range of applications for the systems, compositions, and methods disclosed herein.

Examples of possible variations and modifications to the embodiments disclosed herein can include:

Variations in Spectral Analysis and Image Processing

Dispersion compensation can be calculated in different ways. Any algorithm for dispersion compensation would minimize artifacts in the spectral image. Most algorithms for dispersion compensation use image blurring or sharpness as a measure for optimizing the dispersion compensation. In some embodiments, dispersion compensation can be performed by hardware means such as, for example, by adding either a compensating element on the sample arm and/or by adding an element with equal dispersion on the reference arm of the imaging system.

Normalization by the source spectrum has different ways of reducing the resulting noise. For example, normalizing by a very small value often increases noise. Therefore, it is beneficial to limit the normalization values and not divide by very small numbers. This limit can be done adaptively depending on the image or simply by setting a threshold value.

The number of bands, the sizes of the bands, and/or the location of the bands can be changed. The locations and sizes of the first and second band (in the frequency domain) can be adjusted to optimize the sensitivity for detecting certain spectral entities. In addition, the filters, used to avoid sharp changes in the spectrum, such as Hann or a Gaussian, can be chosen to provide the best results in terms of the spectral and spatial properties of the image.

Construction of the spatial image can be done by matrix multiplication that includes a linear and a quadratic phase. It can also be done by FFT, which is usually faster to compute. In some embodiments, construction of the spatial image can be performed by resampling in the frequency domain.

Balancing of the bands can be done in multiple ways. For example, instead of smoothing the signal difference with a polynomial, different functions or forms of interpolation may be used. In addition, because the origin of the spectral imbalance is intrinsic to the system, it might be possible to calibrate and compensate for it according to the location of the focal plane in the image, This way would not require a spectrally uniform object in the image because the calibration would not be sample dependent, There are multiple ways to display the images. The HSV method can be used, which includes mapping the spectral diff image to the hue and using the saturation and value to highlight objects, such as blood vessels. It is possible to display the images in different ways that will highlight other image features, such as lymph vessels. In some embodiments, other colormaps can also be used such as, but not limited to, isoluminance, Parula, Jet, and/or the like. In addition, it is sometimes beneficial to normalize the spectral diff image by the total signal in the pixel, or by the signal in one of the bands, and obtain a display of the normalized spectral image. This image shows the intrinsic spectral component which is independent of the amount of backscattered light.

Variations in Nanoparticle Development

Numerous sizes of GNRs with varied plasmonic resonance peaks may be used to produce bead-GNR conjugates. Beads of any diameter less than ~10 μm can also be used (beads larger than 10 μm pose biological hazards to living subjects if they are injected intravenously because of their size relative to blood vessels). Additionally, beads made of any number of materials can be used instead of polystyrene. These include (but are not limited to) inorganic compounds, organic polymers, biodegradable materials, and protein-based microbeads. Additional modifications can be made with respect to the biological ligand or antibody chosen to produce molecularly targeted versions of bead-GNR conjugates. In addition, other gold nanoparticles or even non-gold nanoparticles with high optical scattering properties, and (in some embodiments) with sharp optical scattering spectrum, can be used as contrast agents, either alone or in conjunction with the microbeads as previously described.

Variations in Mechanical Design

Figure 7:
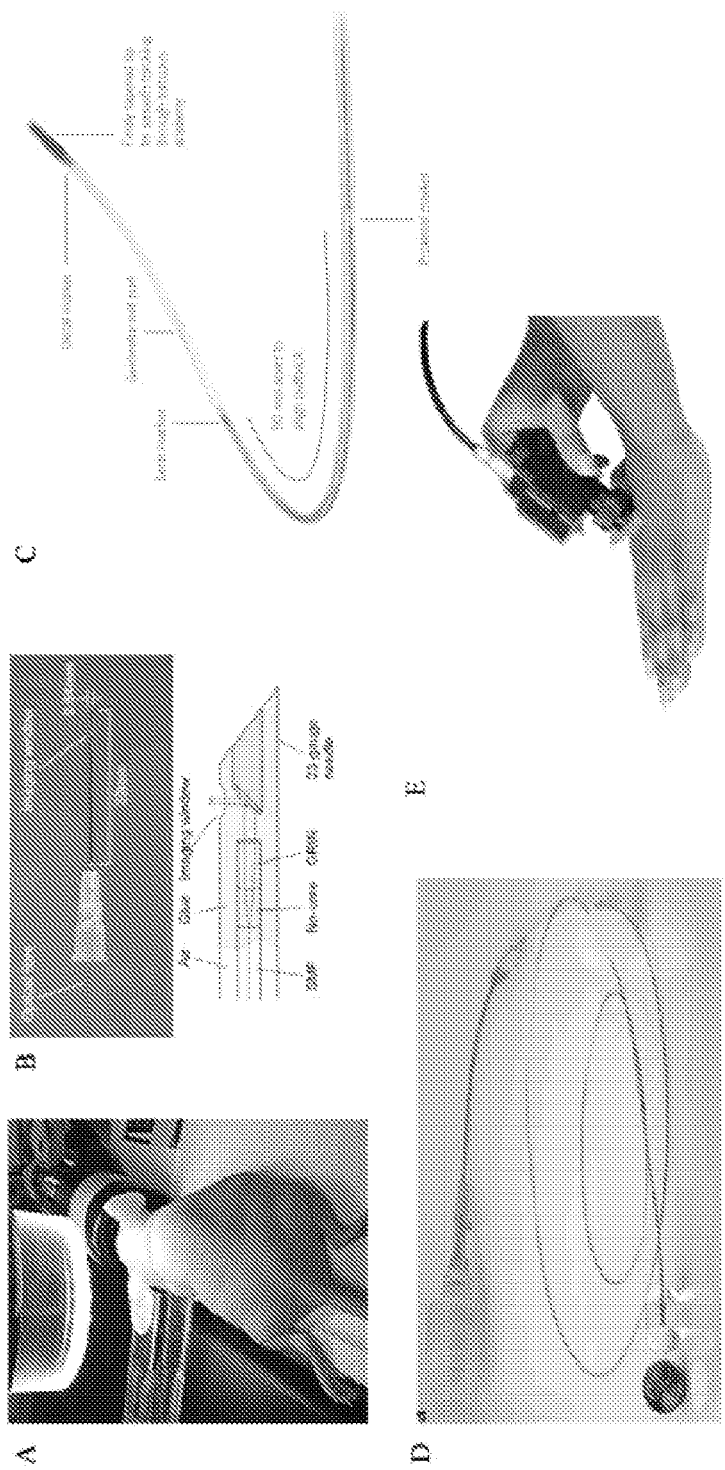
FIG. 7. Alternative optical imaging head designs. A. OCT stand-mounted imaging head. B. Optical Needle Probe. C. Intravascular imaging head. D. Endoscopic imaging head. E. Hand held imaging head.

A variety of mechanical variations in optical head design will allow for additional applications (FIG. 7). Alternative designs include:

OCT stand-mounted imaging scanner head
Optical needle probe
Intravascular probe
Endoscopic probe
Hand held optical scanner A variety of mechanical variations in optical head design can allow for additional applications (FIG. 7).

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, and/or files containing higher-level instructions that are executed by a computer using an interpreter. For example, embodiments may be implemented using C, Java, C++, MATLAB or other programming languages and/or other development tools.

In some embodiments, aspects of the systems and methods disclosed herein can be executed and/or implemented by a computing device including at least a processor and a memory. The processor described herein can be any processor (e.g., a central processing unit (CPU), an application-specific integrated circuit (ASIC), and/or a field programmable gate array (FPGA)) configured to execute one or more instructions received from, for example, a memory. In some embodiments, at least one processor can be a Reduced Instruction Set computing (RISC) processor. Each processor can be in communication with a memory and/or a network card. In some embodiments, each processor can accordingly send information (e.g., data, instructions and/or network data packets) to and/or receive information from a memory and/or a network card.

The memory can be any memory (e.g., a RAM, a ROM, a hard disk drive, an optical drive, other removable media) configured to store information (e.g., one or more software applications, user account information, media, text, etc.). The memory can include one or more modules performing the functions described herein. In some embodiments, the functions described herein can be performed by any number of modules. For example, in some embodiments, the functions described herein can be performed by a single module.

While various embodiments have been described above, it should be understood that they have been presented by way of example, and not limitation. Where methods described above indicate certain events occurring in certain order, the ordering of certain events can be modified. Additionally, certain of the events may be performed concurrently in a parallel process when possible, as well as performed sequentially as described above.

EXAMPLE 1

Gold nanorods (GNRs) are often stabilized with polyethylene glycol (PEG) prior to use in biomedical applications. It was found that while small GNRs (~50×15 nm) benefited from PEG coating, larger than usual PEG-coated GNRs (~90×30 nm) rapidly aggregated in solution, suggesting size-dependent physical mechanisms of GNR stability. Provided herein is method for functionalizing large GNRs in water and biological scrum, allowing one to harness their enhanced optical properties due to greater cross-sectional area. Also provided herein is a method to conjugate large GNRs with biomolecules, enabling particle binding to biological targets of interest. Finally, optical coherence tomography (OCT) was used to demonstrate that large GNRs offer increased signal relative to small GNRs in optical imaging techniques. These studies not only illuminate a novel size-dependent GNR stability phenomenon but also provide demonstration of practical applications of large GNRs in biological study.

Based on theoretical modeling, large GNRs are predicted to have advantages including greater absorption and extinction coefficients, as well as enhanced scattering cross-sections relative to their commonly-used smaller counterparts in numerous biomedical imaging techniques.

To explore whether large GNRs can be successfully adapted for biological studies, the stability of small (~50×15 nm) and large (~90×30 nm) GNRs as a function of surface coating was compared. It was found that conventional PEG surface coating does not stabilize large GNRs, however the polyelectrolyte poly(sodium 4-styrenesulfonate) conferred excellent stability to large GNRs. A method was developed to further functionalize PSS-coated large GNRs (hence called Large GNRs-PSS) with biological ligands of interest. Optical coherence tomography (OCT) was used to show that large GNRs produce greater optical signals than small GNRs. This work not only underscores the relation between nanoparticle size and stability but also offers key practical improvements to current biological applications of GNRs.

Figure 8:
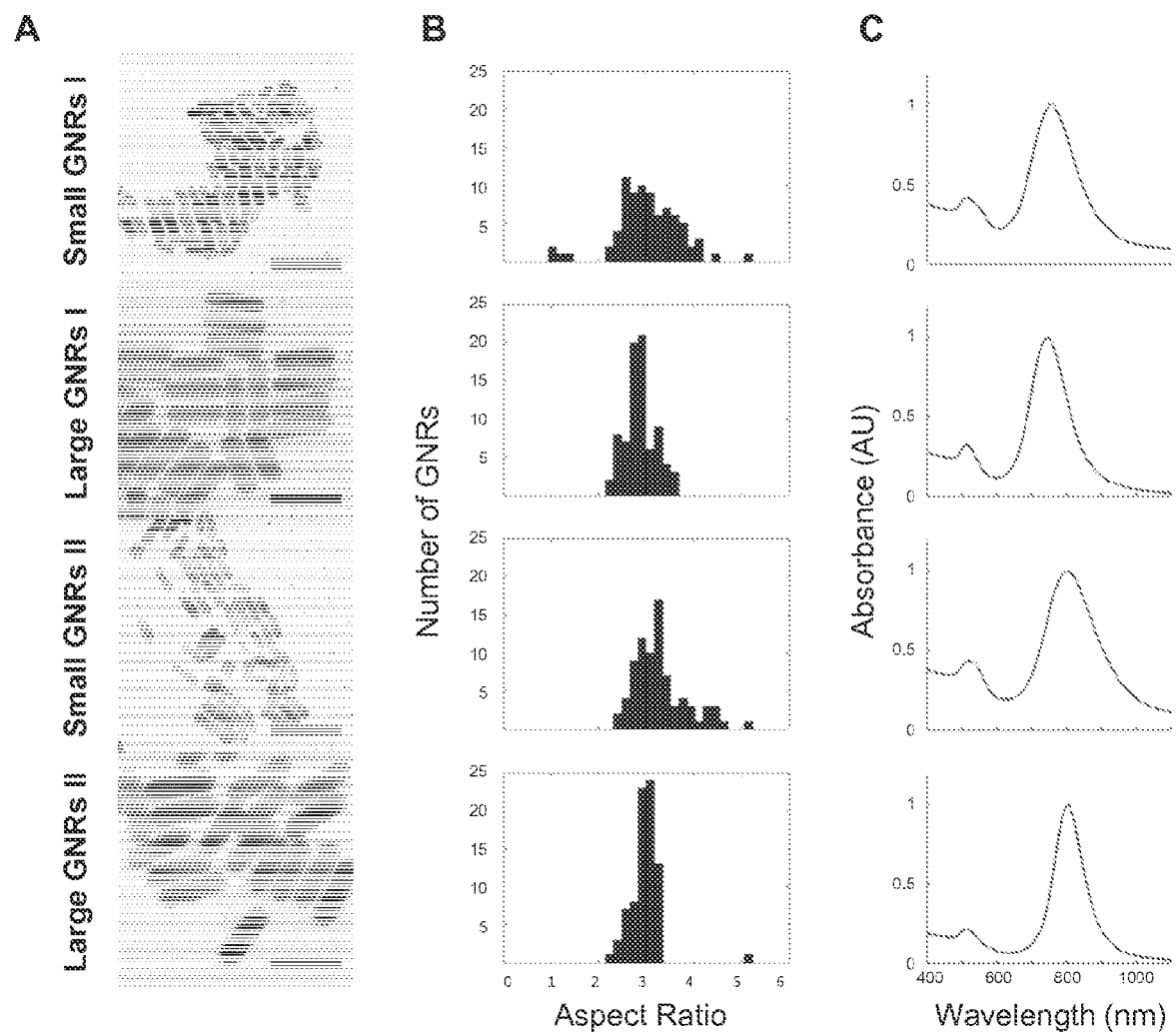
FIG. 8. Initial GNR characterization. A) TEM images of Small GNRs I (length: 48±6 nm, width: 15±3 nm), Small GNRs II (length: 45±7 nm, width: 14±2 nm) produced by the El-Sayed method and Large GNRs I (length: 88±10 nm, width: 32±4 nm), Large GNRs II (length: 93±7 nm, width: 33±1 nm) produced by the Murray method (all scale bars=100 nm). All TEM images were originally acquired at 20,000× magnification and cropped to the same area to preserve relative comparisons between particle sizes. B) Particle aspect ratio (AR) distributions for small and large GNR batches (n=80 for each batch) were also determined. Small GNRs I AR: 3.1±0.6, Large GNRs I AR: 2.9±0.3, Small GNRs II AR: 3.3±0.6, and Large GNRs II AR: 3.0±0.3 C) Absorbance spectra of each GNR batch. Small GNRs I LSPR: 756 nm, Large GNRs I LSPR: 744 nm, Small GNRs II LSPR: 802 nm, and Large GNRs II LSPR: 804 nm.

Small and large GNRs were synthesized and characterized with Transmission Electron Microscopy (TEM), Vis-NIR Spectrometry, and Electrophoretic Light Scattering (ELS, i.e., zeta potential). FIG. 8A depicts small (~50×15 nm) and large (~90×30 nm) GNRs that were synthesized using methods described by El-Sayed and Murray respectively. Although different in physical size, pairs of large and small GNRs with similar plasmonic resonances (I: ~750 nm and II: ~800 nm, FIG. 8C) were chosen for accurate spectral comparisons of stability. Interestingly, large GNRs exhibit greater monodispersity than small GNRs as evidenced by particle size distributions (FIG. 8B).

Figure 9:
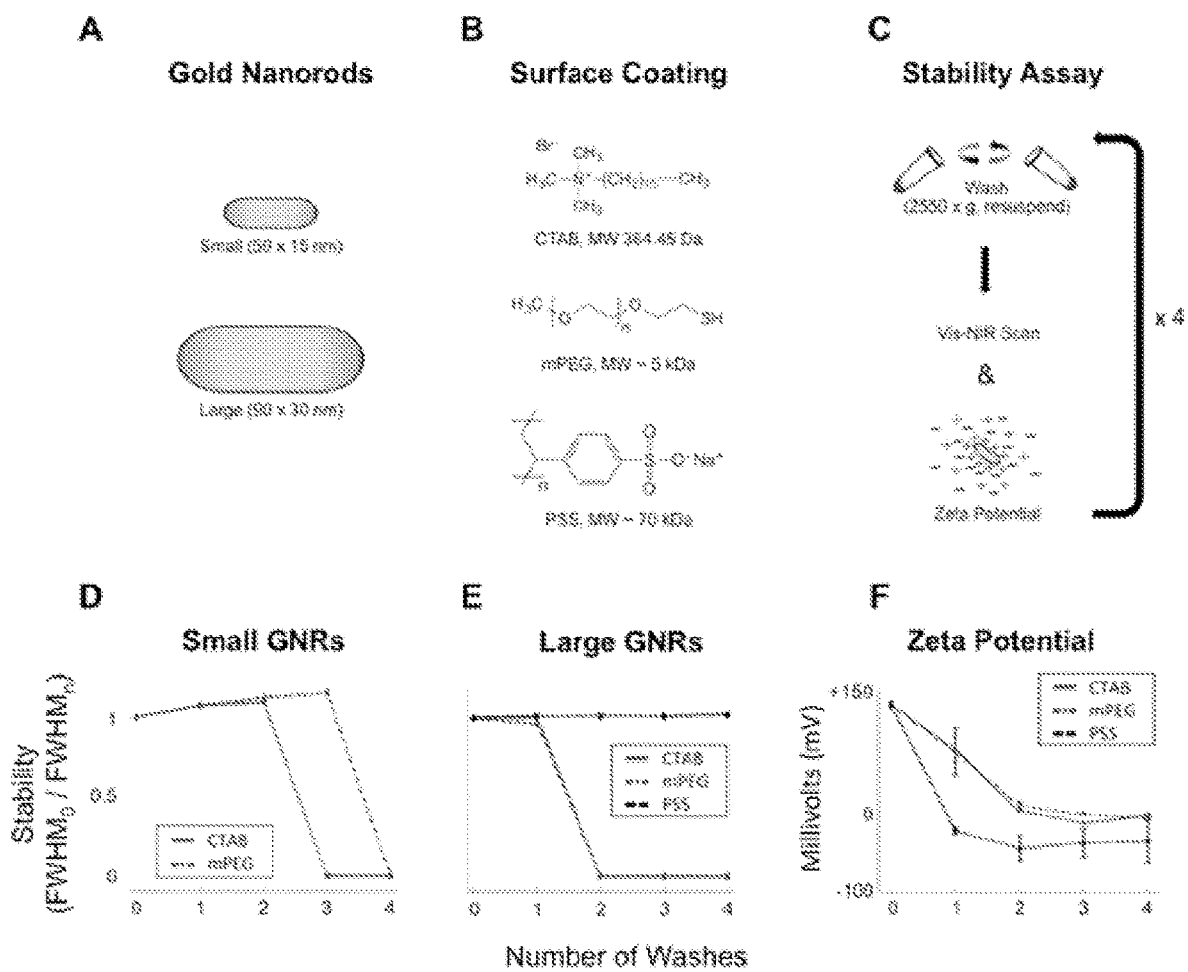
FIG. 9. Characterization of GNR stability trends as a function of size and surface coating. Small and Large GNRs (A) were initially characterized by Vis-NIR spectrometry and Zeta Potential and then prepared with one of three different surface coating molecules (B). Coated GNRs were then subjected to four rounds of washing and analyzed by Vis-NIR spectrometry and Zeta Potential after each wash to determine particle stability (C). Particle stability was measured as spectral peak broadening by dividing absorbance peak full width at half maximum before washing ($FWHM_0$) by peak full width at half maximum after each of four washes ($FWHM_n$, where n=1-4). (D) depicts the stability of Small GNRs-CTAB and Small GNRs-mPEG (Batch II). (E) depicts the stability of Large GNRs-CTAB, Large GNRs-mPEG, and Large GNRs-PSS (Batch II). Zeta potential measurements for Large GNRs II (F) are consistent with the stability trends characterized in E, and they also provide validation of successful surface coating. Error bars represent standard error of the mean calculated from triplicate measurements.
Figure 16:
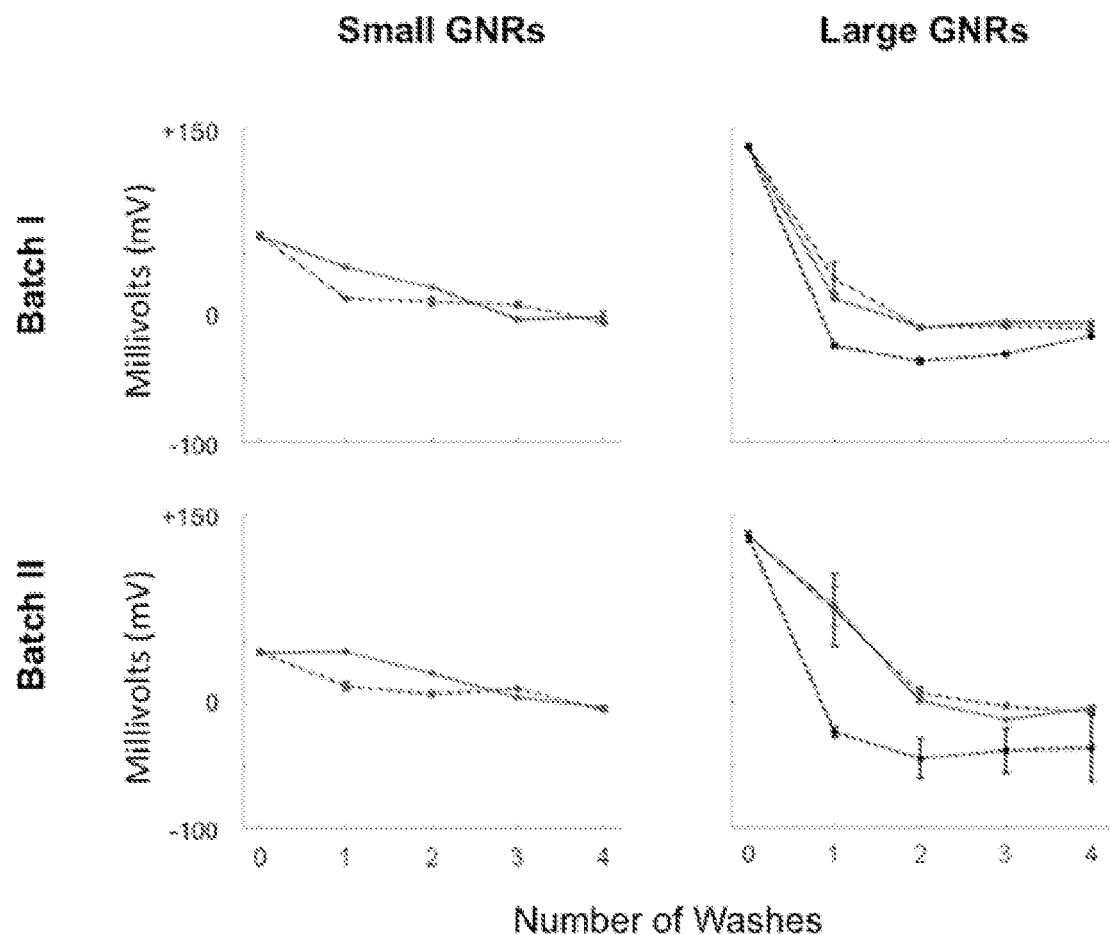
FIG. 16. Zeta potential as a function of number of washes, particle size, and coating. All zeta potential measurements were performed in triplicate. Error bars represent standard error of the mean (s.e.m.) for each set of three measurements.

GNRs were prepared with one of three surface coatings: CTAB, mPEG-SH (MW ~5 kDa), or PSS (MW ~70 kDa), resulting in GNRs-CTAB, GNRs-mPEG, and GNRs-PSS, respectively. Coated particles were then washed through multiple rounds of centrifugation (FIGS. 9A-C). FIG. 9 shows trends in GNR absorbance spectra, which is a proxy for colloidal stability/aggregation, as a function of surface coating and number of wash cycles (FIGS. 9D-E). As expected based on previous reports, GNRs-CTAB synthesized by either method aggregated after minimal washing by centrifugation (FIGS. 9D-E, FIGS. 14-15). Large GNRs-CTAB aggregated after two rounds of washing while Small GNRs-CTAB aggregated after three rounds. While Small GNRs-mPEG remained stable for an additional wash relative to Small GNRs-CTAB, large GNRs-mPEG experienced no such increase in stability. Unlike Large-GNRs-mPEG, Large GNRs-PSS exhibited marked improvements in stability (FIG. 9E). Zeta potential measurements (FIGS. 9F, 16, and Table 1) indicate a rapid shift from positive to negative surface potential for Large GNRs-CTAB incubated with PSS, consistent with polyelectrolytic overcoating. There was no observation of spectral broadening for large GNRs upon addition of PSS or after washing, although such an effect has been reported for small GNRs. Previous reports have already demonstrated that PSS can be used to stabilize small GNRs in water. These findings indicate that conventional PEG-based methods for GNR surface coating are insufficient to confer stability in aqueous solutions for GNRs in different size regimes.

TABLE 1

Original zeta potential measurements
(presented as mean from triplicate measurements ± s.e.m.)

| GNR | Wash # | CTAB | mPEG | PSS |
|---|---|---|---|---|
| Small GNRs I | 0 | +64 +/− 1.9 mV | — | — |
|  | 1 | +39 +/− 0.7 mV | +14 +/− 0.8 mV | — |

TABLE 1-continued

Original zeta potential measurements
(presented as mean from triplicate measurements ± s.e.m.)

| GNR | Wash # | CTAB | mPEG | PSS |
|---|---|---|---|---|
| | 2 | +23 +/− 0.6 mV | +11 +/− 3.3 mV | — |
| | 3 | −2.8 +/− 0.6 mV | +9.1 +/− 2.2 mV | — |
| | 4 | −1.0 +/− 5.2 mV | −5.2 +/− 0.5 mV | — |
| Small GNRs II | 0 | +40 +/− 1.0 mV | — | — |
| | 1 | +41 +/− 0.8 mV | +13 +/− 3.3 mV | — |
| | 2 | +23 +/− 0.3 mV | +6.9 +/− 1.9 mV | — |
| | 3 | +4.4 +/− 0.7 mV | +11 +/− 1.0 mV | — |
| | 4 | −3.4 +/− 0.5 mV | −5.4 +/− 1.4 mV | — |
| Large GNRs I | 0 | +135 +/− 1.7 mV | — | — |
| | 1 | +14 +/− 0.9 mV | +30 +/− 13 mV | −24 +/− 1.0 mV |
| | 2 | −8.8 +/− 1.7 mV | −8.7 +/− 0.4 mV | −36 +/− 2.3 mV |
| | 3 | −4.9 +/− 0.6 mV | −8.0 +/− 1.1 mV | −30 +/− 1.5 mV |
| | 4 | −5.4 +/− 1.0 mV | −10 +/− 2.9 mV | −16 +/− 1.2 mV |
| Large GNRs II | 0 | +132 +/− 4.3 mV | — | — |
| | 1 | +77 +/− 16 mV | +73 +/− 29 mV | +24 +/− 4.1 mV |
| | 2 | +1.2 +/− 0.9 mV | +7.3 +/− 4.3 mV | −45 +/− 16 mV |
| | 3 | −14 +/− 0.4 mV | −3.2 +/− 0.7 mV | −39 +/− 18 mV |
| | 4 | −4.0 +/− 0.8 mV | −8.0 +/− 1.9 mV | −37 +/− 27 mV |

Figure 10:
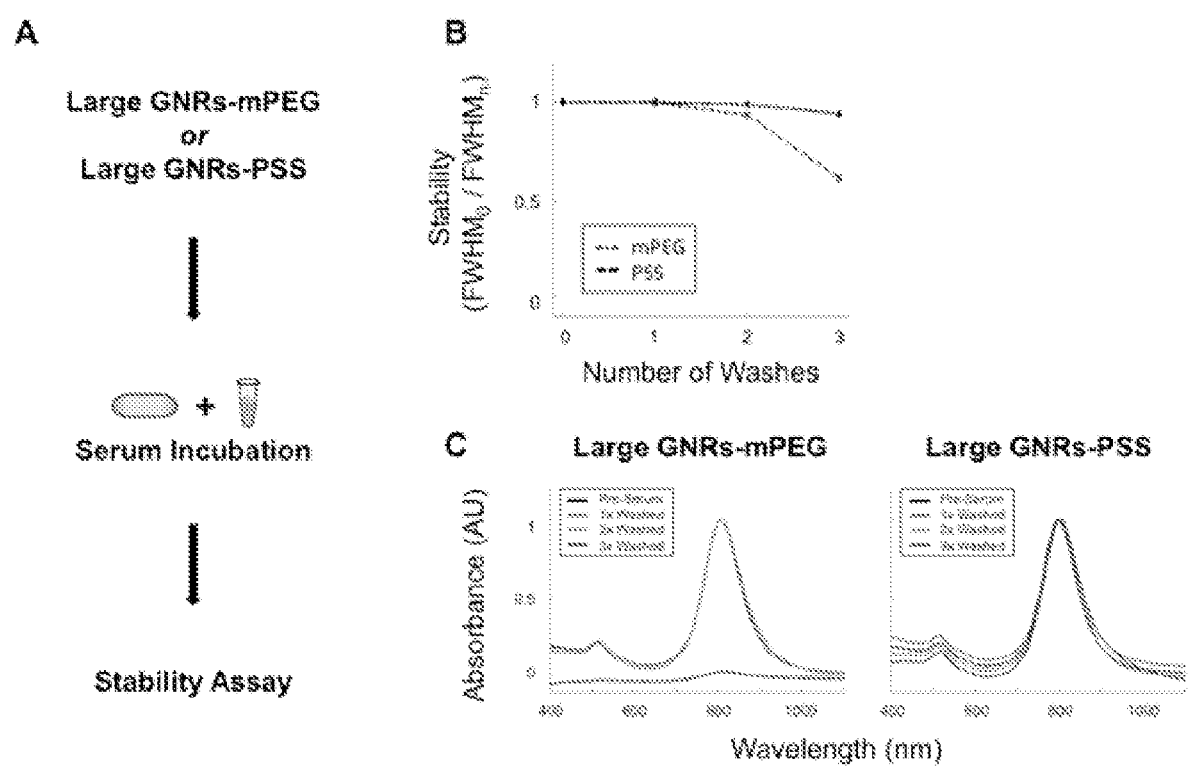
FIG. 10. Large GNR are stable in biological serum. A) Large GNRs-mPEG and Large GNRs-PSS were prepared, incubated with fetal bovine serum (FBS) for 3 h, and subjected to three rounds of washing by centrifugation. The absorbance spectrum of each GNR type was taken after each wash to assess serum stability. B) Measurements of absorbance peak $FWHM_0/FWHM_n$ demonstrate that Large GNRs-PSS are more stable in biological serum than Large GNRs-mPEG. C) Raw absorbance spectra for each particle type demonstrate this difference in stability more clearly, as Large GNRs-mPEG exhibit virtually no plasmonic peak after the third wash. Unlike Large GNRs-mPEG, Large GNRs-PSS exhibit little change in terms of absorbance properties.

The next test was whether Large GNRs-PSS remain stable in biologically-relevant environments. Large GNRs-mPEG and Large GNRs-PSS were prepared as 1 mL aliquots and incubated with 500 μL FBS (FIG. 10A). Absorbance measurements indicate that large GNRs-PSS remain stable during and after incubation with FBS followed by washing. Interestingly, Large GNRs-mPEG incubated with FBS are stable after two washes (FIG. 10B-C) while Large GNRs-mPEG in water are stable for only one wash (FIG. 9E). It is possible that adsorbed FBS (the so-called "protein corona") is responsible for this extended stability. Spectral broadening indicative of aggregation occurred after the third wash for Large GNRs-mPEG but not for Large GNRs-PSS (FIG. 10B-C). This result suggests that Large GNRs-PSS remain stable even after excess FBS is washed away.

Figure 11:
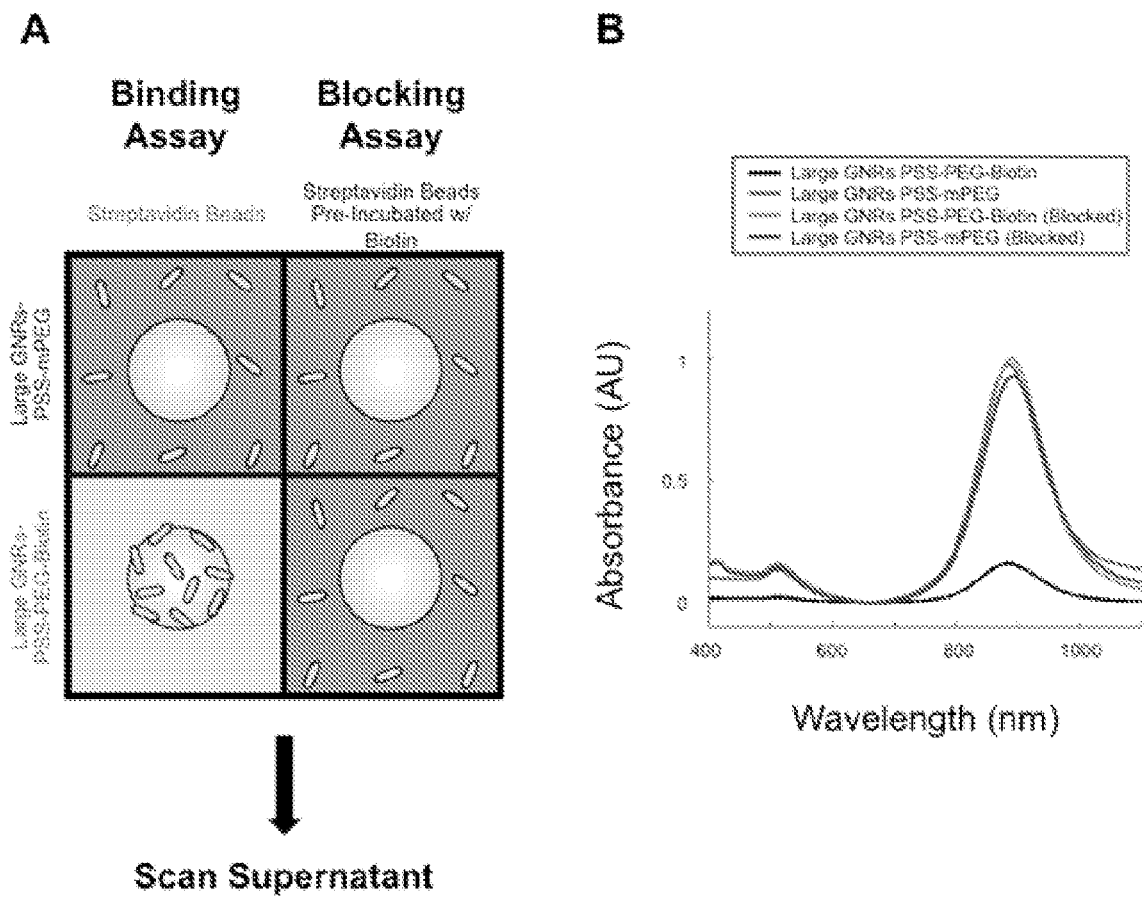
FIG. 11. Large GNRs-PSS retain specific binding functionality. Large GNRs-PSS-PEG-Biotin and Large GNRs-PSS-mPEG were prepared and incubated with FBS to mimic biological environments. A) FBS-incubated GNRs were then used in the biotin-streptavidin binding and blocking assays. For the binding assay, Large GNRs-PSS-PEG-Biotin and Large GNRs-PSS-mPEG were incubated with streptavidin-coated polystyrene beads (3 µm diameter) and centrifuged for 10 s at 1000×g to separate beads from free GNRs. The same process was repeated in the blocking assay, except that the streptavidin-coated beads were pre-incubated with excess free biotin to preclude specific binding of Large-GNRs-PSS-PEG-Biotin. B) Absorbance measurements of the supernatant from each of the four bead-GNR combinations were taken after incubation. The same concentration of GNRs (OD 1) was used in each incubation, but only the supernatant from the incubation of Large GNRs-PSS-PEG-Biotin and streptavidin beads exhibits a significant decrease in GNR concentration. These results demonstrate the proof of principle that Large GNRs-PSS can be functionalized with ligands that retain molecular binding specificity in the presence of non-specific proteins, which will be advantageous for eventual applications to in vivo molecular imaging.
Figure 17:
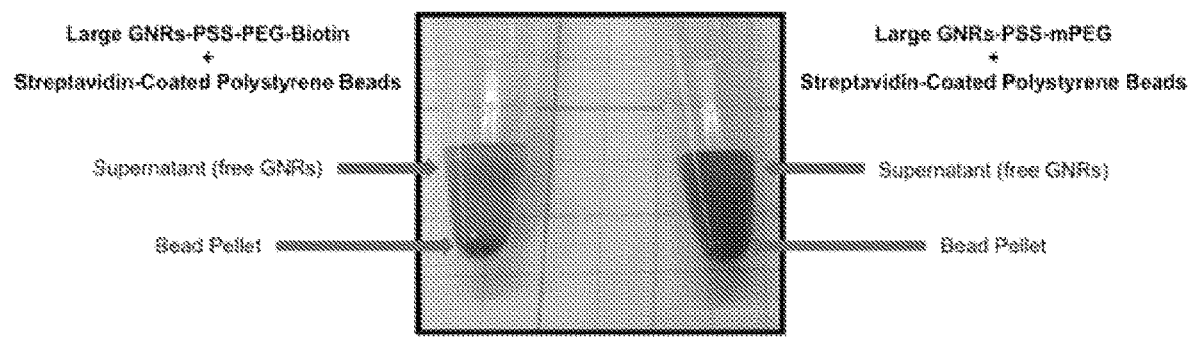
FIG. 17. Qualitative visual assessment of GNR-bead binding and blocking assays. A) Large GNRs-PSS-PEG-Biotin bind streptavidin-coated beads, resulting in a red bead pellet and reduced GNR concentration in the supernatant. Large GNRs-PSS-mPEG are incapable of specific binding to streptavidin coated beads, and the majority of these GNRs remain free in solution rather than bound to beads in the pellet. B) Washing bead pellets post-incubation further demonstrates the binding specificity of Large GNRs-PSS-PEG-Biotin. The red pellet is clearly visible for the Large GNRs-PSS-PEG-Biotin+streptavidin bead incubation while the pellet remains white when GNRs lack a biotin coating (left). No red pellet occurs for either GNR type if the streptavidin beads are pre-blocked with free biotin (right).
Figure 17:
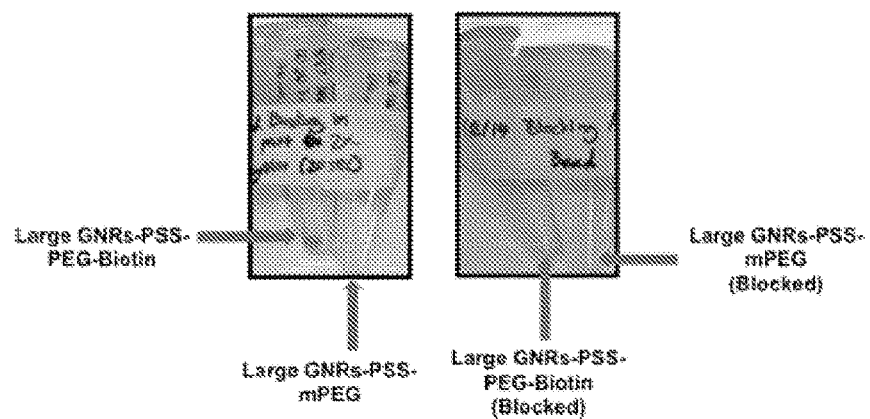
Figure 18:
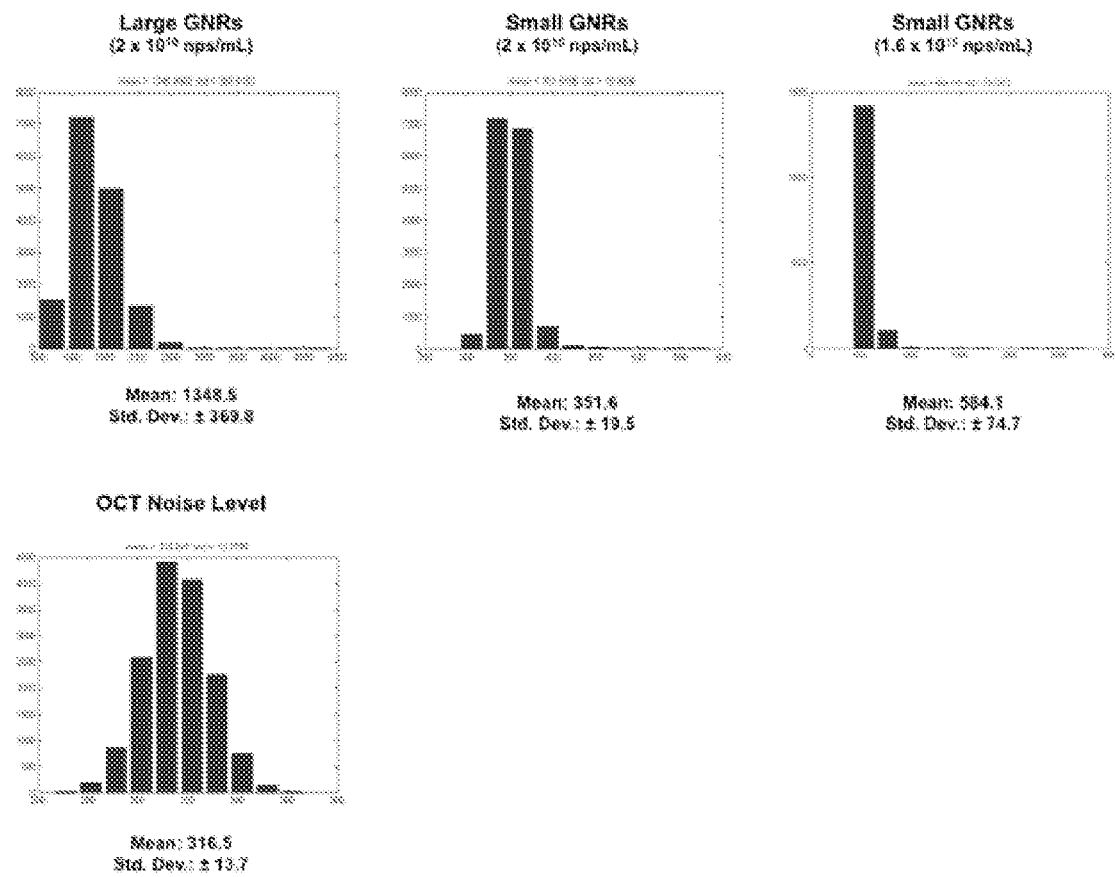
FIG. 18. Pixel intensity distributions and mean OCT signal±standard deviation of large and small GNRs from analyzed regions of interest (ROIs, n=15,000 pixels each). This data was used to calculate statistical significance and relative OCT signal strength for large and small GNRs at equivalent concentrations (OD and nps/mL). The OCT system's noise level was also quantified. All ROIs were taken at the same focal depth and relative location within GNR sample tubes to minimize aberrant differences in signal intensity.
Figure 19:
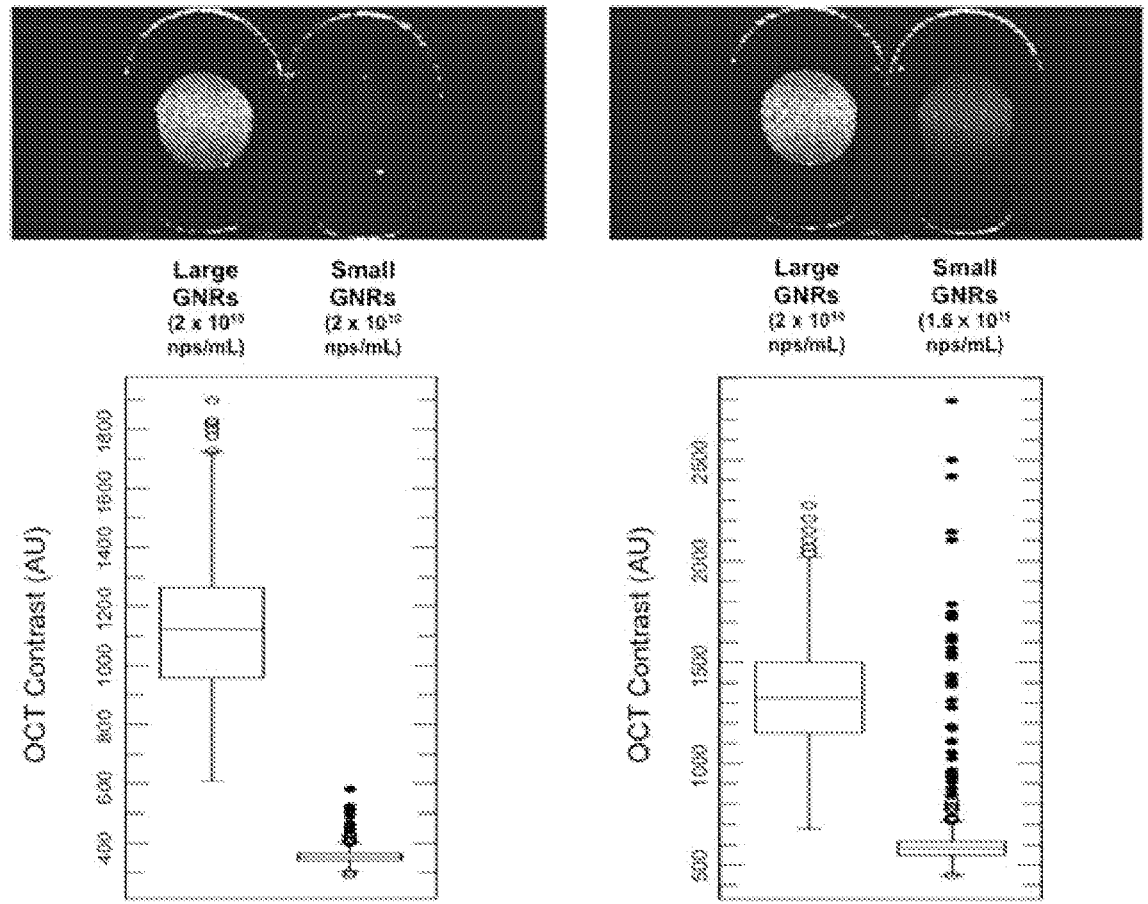
FIG. 19. Original OCT images of Large vs Small GNRs at equivalent nps/mL (left) and equivalent OD (right). 600 pixel subsets of the original 15,000 pixel ROIs were taken from each sample to determine the statistical significance of the difference in signal between large and small GNRs. Two-tailed Student's t-tests were performed to compare Large vs Small GNRs in each case. Box plots from each comparison are presented below their respective OCT images. In each case, OCT signal from Large GNRs is markedly greater than from Small GNRs (p<0.0001).

Several previous reports describe conjugation of antibodies to Small GNRs-PSS through electrostatic adsorption. While these methods are functional, covalent chemistry is often desirable for biological applications because covalent bonds are more stable than electrostatic adhesions in biological fluids. Furthermore, specific chemistry can be used to bind biomolecules such as antibodies at specific functional groups rather than generic electrostatic patches. A method was tested for conjugating biological molecules to Large GNRs-PSS through specific interactions rather than electrostatic adsorption. Large GNRs-PSS were incubated with either mPEG-SH or Biotin-PEG-SH and washed 2× to remove excess reagents (resulting in Large GNR-PSS-mPEG and Large GNR-PSS-PEG-Biotin, respectively). Large GNRs-PSS-PEG-Biotin and Large GNRs-PSS-mPEG were further incubated with FBS to mimic biological environments and then mixed with streptavidin-coated polystyrene beads in water. Because of the high affinity interaction between biotin and streptavidin, we hypothesized that Large GNRs-PSS-PEG-Biotin would bind to the beads while Large GNRs-PSS-mPEG would remain free in solution (FIG. 11A, "Binding Assay"). After 20 seconds of centrifugation at 1000×g, a dark red pellet of Large GNRs-PSS-PEG-Biotin/streptavidin bead aggregates and streptavidin beads was observed, and the color of the supernatant (presumably containing unbound GNRs) was markedly clear. In contrast, the pellet from the Large GNRs-PSS-mPEG incubation was white (the color of beads only) and the supernatant from this incubation remained very red, indicating the presence of GNRs in solution (FIG. 17A). After washing beads post-incubation, a clear difference in bead pellet color is observed for streptavidin beads incubated with Large GNRs-PSS-PEG-Biotin versus Large GNRs-PSS-mPEG in FBS (FIG. 17B). This difference indicates that Large GNRs-PSS-PEG-Biotin bind with specificity to streptavidin coated beads even in the presence of FBS while Large GNRs-PSS-mPEG do not. Furthermore, blocking the streptavidin-coated beads with free biotin prior to GNR incubation (FIG. 11A, "Blocking Assay") prevented Large GNRs-PSS-PEG-Biotin binding (no red color in the pellet) while the Large GNRs-PSS-mPEG result remained the same as in the unblocked condition (FIG. 17B). To confirm visual assessments of the binding and blocking assays, we measured absorbance spectra for supernatants from blocked and unblocked incubation conditions. Despite using equivalent amounts of GNRs in each incubation, a much higher concentration of Large GNRs-PSS-mPEG remained in solution (i.e., not in the bead pellet) compared to Large GNRs-PSS-PEG-Biotin (FIG. 11B). This result indicates that more Large GNRs-PSS-PEG-Biotin are removed from solution (i.e., bind to beads) than Large GNRs-PSS-mPEG upon incubation with streptavidin-coated beads. However, pre-incubation of the streptavidin beads with free biotin abrogated this effect (FIG. 11B), suggesting that the observed interaction of Large GNRs-PSS-PEG-Biotin and streptavidin beads is molecularly specific (i.e., due to the biotin-streptavidin interaction and not non-specific binding). The results of the binding and blocking assays collectively indicate that 1) PEG-SH reagents are capable of binding the surface of Large GNRs-PSS and 2) heterobifunctional PEG molecules (e.g., Biotin-PEG-SH) can be conjugated to Large GNRs-PSS to enable subsequent specific conjugation with biological ligands (e.g., antibodies) of interest even in the presence of non-specific proteins.

Figure 12:
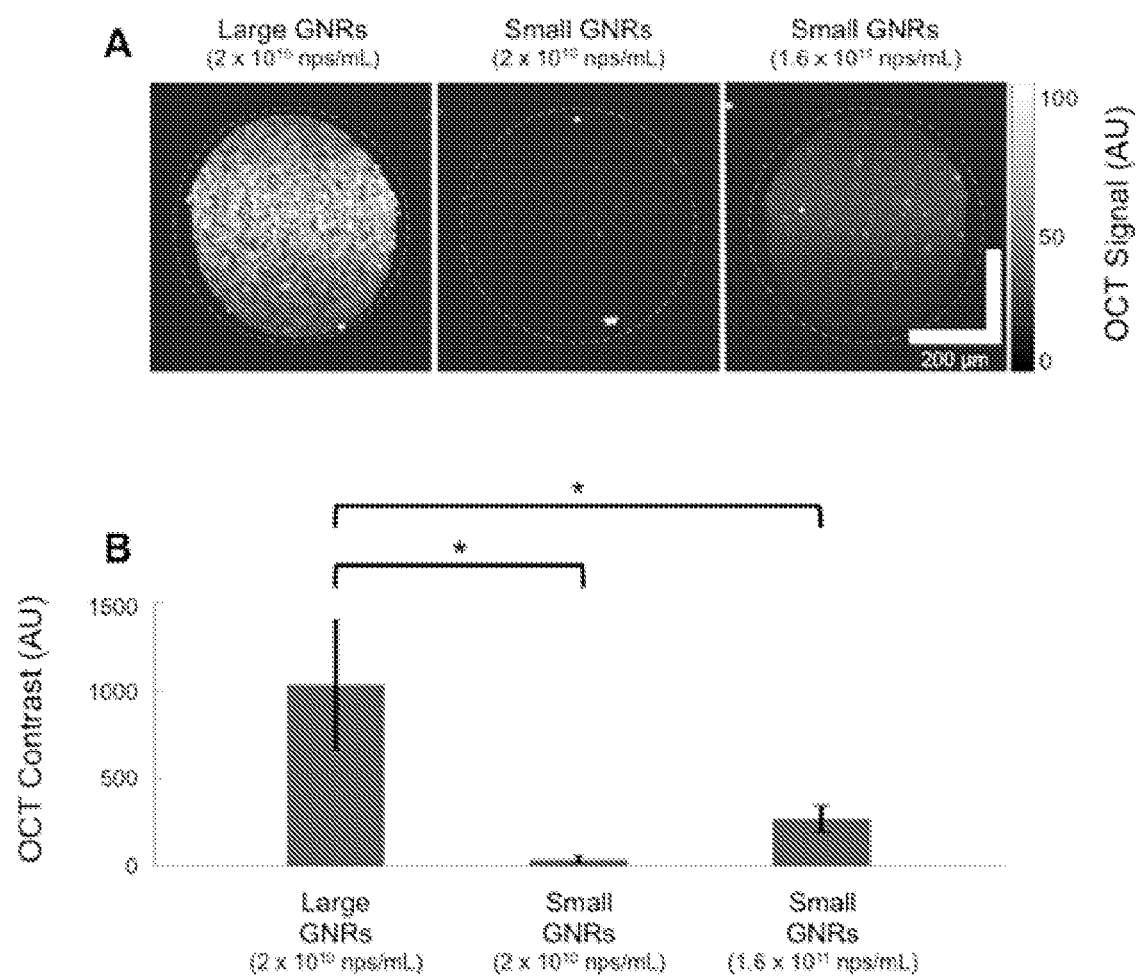
FIG. 12. Large GNRs are more effective OCT contrast agents than Small GNRs. A) Linear-scale OCT B-scans of Large GNRs II (left: OD $1/2 \times 10^{10}$ nps/mL) and two concentrations of Small GNRs II (middle: OD $0.125/2 \times 10^{10}$ nps/mL and right: OD $1/1.6 \times 10^{11}$ nps/mL) show that large GNRs scatter significantly more near-infrared light than small GNRs of equivalent plasmonic properties both for a given optical density (OD 1) and on a per nanoparticle basis ($2 \times 10^{10}$ nps/mL). B) Region of interest analysis shows that Large GNRs exhibit ~4× greater scattering that Small GNRs at the same OD (two-tailed Student's t-test, p<0.0001). OD 1 Small GNRs must be diluted 8× to OD 0.125 to reach the same concentration of OD 1 Large GNRs in terms of nps/mL. The OCT signal from $2 \times 10^{10}$ nps/mL is too close to the noise threshold to compare to large GNRs in a statistically meaningful manner. However, the required dilution factor (8×) and the ~4× greater signal from the equivalent OD comparison suggest that Large GNRs may produce up to ~32× greater OCT contrast than Small GNRs per particle.
Figure 13:
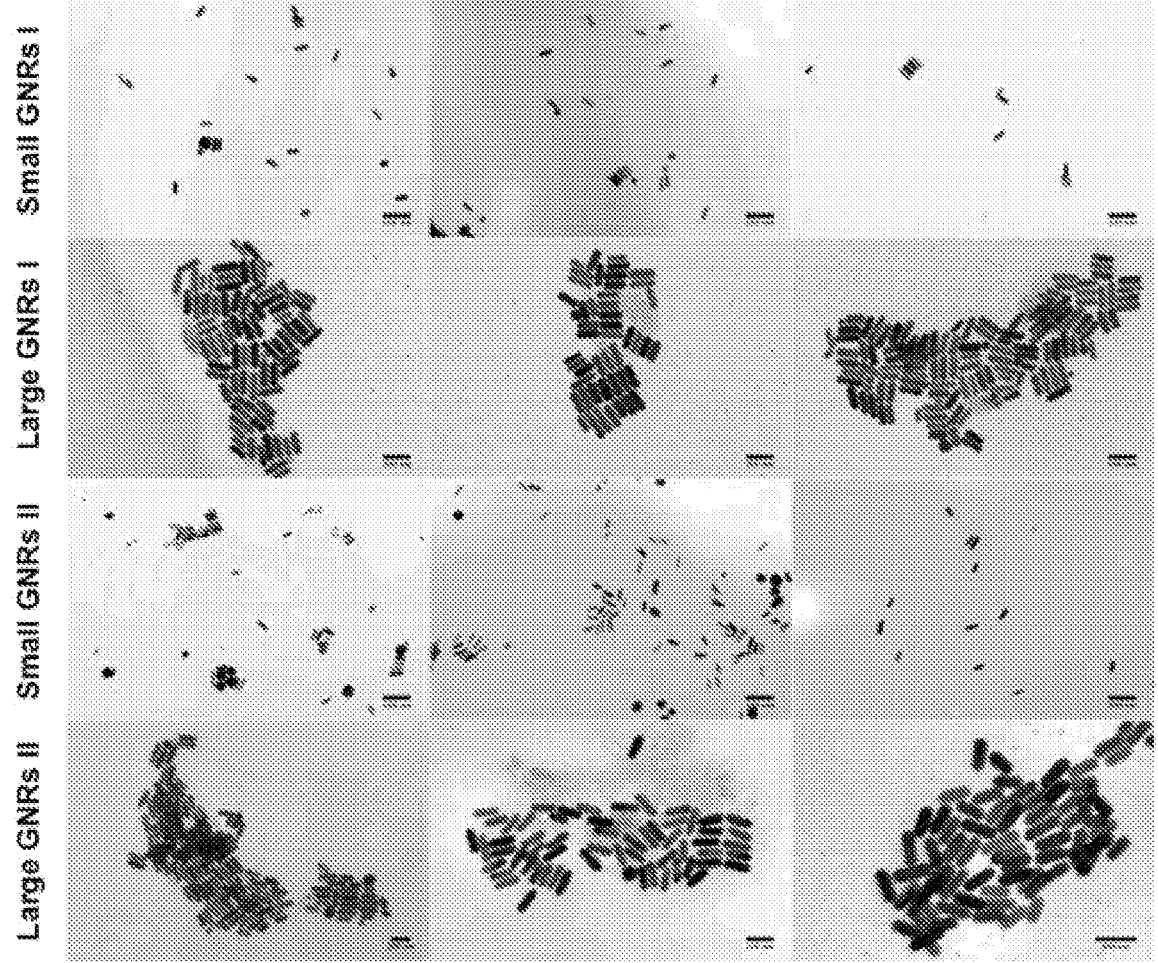
FIG. 13. Additional TEM images used to calculate average GNR dimensions and aspect ratios. All scale bars are 100 nm.
Figure 14:
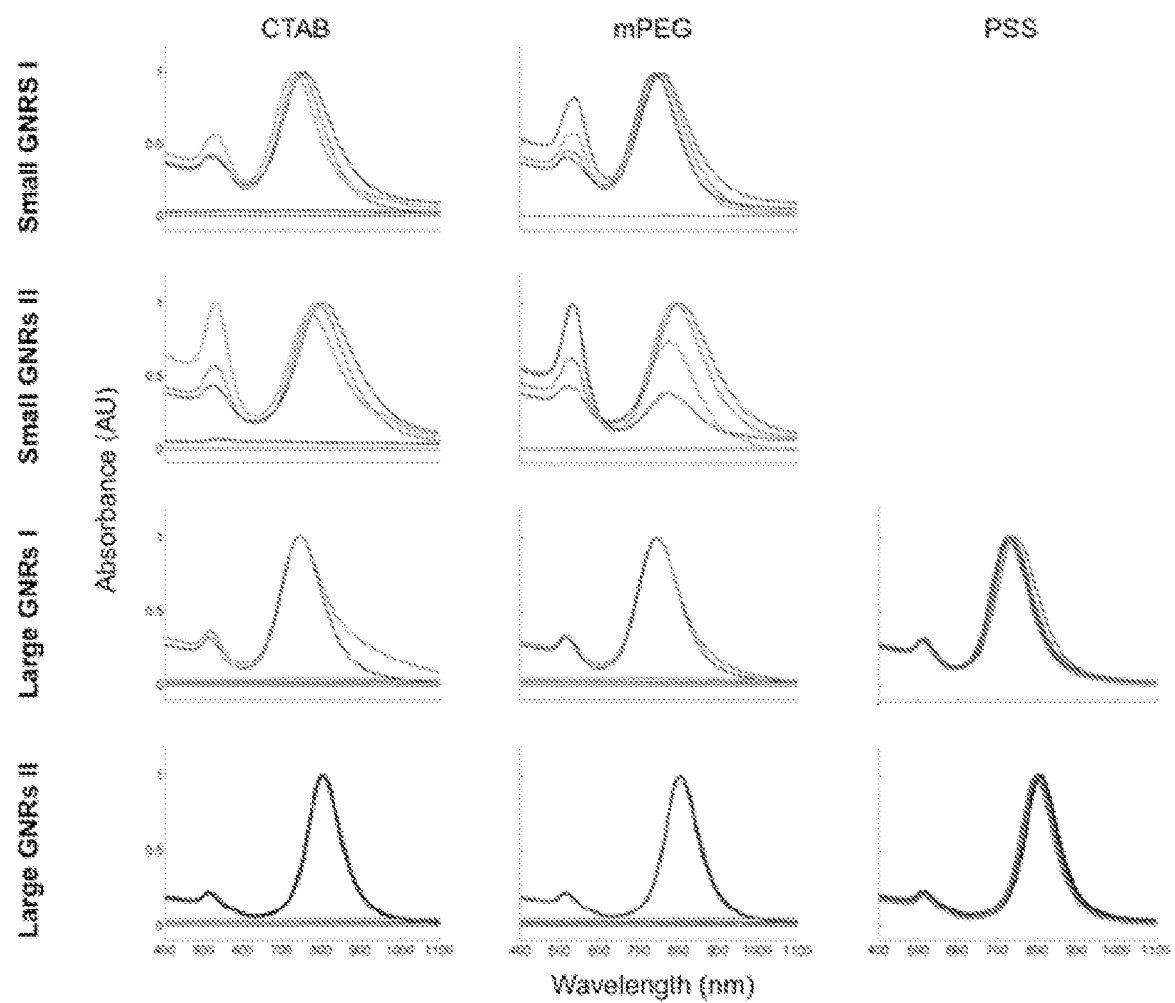
FIG. 14. Original raw absorbance spectra measured for all GNRs, coatings, and wash cycles. Stability plots of $FWHM_0/FWHM_n$ were derived from this data. Each plot contains the spectra from 0× wash (black), 1× wash (red), 2× wash (green), 3× wash (blue), and 4× wash (magenta) steps for the given particle size and coating. Absorbance spectra are peak normalized to account for material loss through pipetting and to clearly show when a given particle completely crashes out of solution (denoted by flat line).
Figure 15:
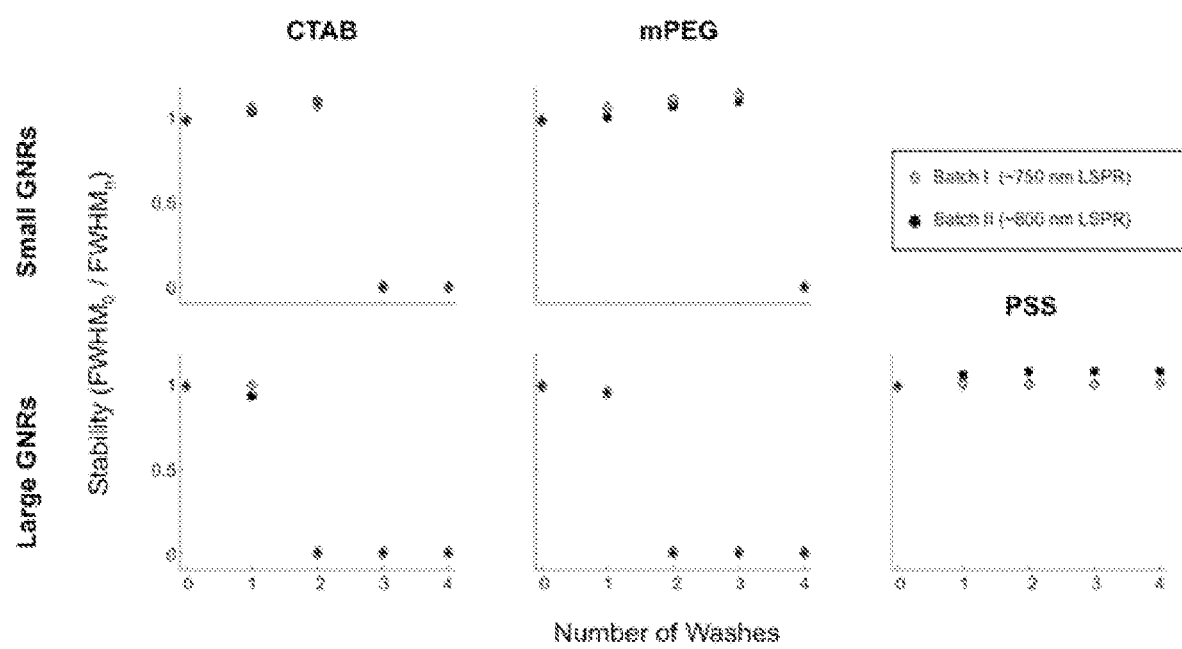
FIG. 15. $FWHM_0/FWHM_n$ stability plots for all GNRs used in this study. Note that stability trends for a given particle size and coating are consistent for Batch I and Batch II and thus independent of plasmonic properties.

In addition to developing novel methods to prepare large GNRs for biological applications, we sought to demonstrate that large GNRs have favorable optical properties when compared to small GNRs. To demonstrate some of the potential strengths of large GNRs for biomedical imaging, we acquired images of large and small GNRs using OCT. Small and large GNRs were prepared to 1) equal optical density (OD 1) and 2) equal particle concentration ($2 \times 10^{10}$ nps/mL) in glass capillary tubes. FIG. 12A depicts the relative OCT signal from each GNR sample. FIG. 12B shows that OD 1 large GNRs exhibit ~4× greater OCT contrast (defined as raw OCT signal minus raw OCT noise) than OD 1 small GNRs (p<0.0001, see FIGS. S18-19). This result indicates scattering constitutes a greater proportion of the total absorbance of large GNRs than small GNRs. It is interesting to note that OD 1 large GNRs are ~8× lower in particle concentration ($2 \times 10^{10}$ nps/mL) than OD 1 small GNRs ($1.6 \times 10^{10}$ nps/mL). Because of this difference, a comparison was made between the signals of equal numbers of large GNRs and small GNRs. While the signal from $2 \times 10^{10}$ nps/mL small GNRs was higher than the OCT noise level, this difference was not statistically significant. However, based on the 4× greater signal of large GNRs versus small GNRs for equivalent OD and the 8× dilution of OD 1 small GNRs required to achieve equal nps/mL, it is expected that large GNRs may produce up to ~32× greater OCT contrast than small GNRs on a per particle basis. These results indicate that small GNRs may be replaced by large GNRs in existing biomedical imaging approaches to improve achievable signal-to-noise ratios (SNR).

Another finding from this study is that GNRs of larger-than-conventional sizes cannot be sufficiently stabilized by one of the most commonly-implemented surface modification methods (PEGylation). This result implies that there can be a nanoparticle size threshold above which certain surface coatings are ineffective. For larger GNRs, the steric mechanism of stability conferred by PEG chains cannot prevent particle aggregation while electrostatic repulsion via PSS can provide the required stability.

Large GNRs-PSS are expected to remain stable if used in vivo. This is based on the observation that Large GNRs-PSS incubated with FBS remained highly stable through incubation and washing steps (FIGS. 10B-C). This observation is somewhat contradictory to a previous report in which Small GNRs-PSS exhibited instability in serum. However this difference could be due in part to the different molecular weights of the PSS polymers used in the cited report (MW ~15 kDa) and our study (MW ~70 kDa). Larger PSS polymers contain more anions per molecule and may benefit from avidity effects when bound to the GNR-CTAB surface, thereby enhancing stability during and after washing.

A highly advantageous characteristic for a biomedical nanoparticle is the ability to bind specific molecular targets of interest. Molecular specificity is enabled by the use of a surface coating that can be further conjugated with biological ligands or antibodies. Ideally, molecular targeting moieties can be linked to the nanoparticle through covalent bonds or high-affinity biomolecule interactions. Our proof of concept binding experiments with Large GNRs-PSS-PEG-Biotin and streptavidin beads show that Large GNRs-PSS can be functionalized with such biological ligands. Through this demonstration, we have developed a novel platform for producing molecularly-targeted GNR contrast agents. It is conceivable that biotinylated GNRs can be further conjugated with a variety of biological ligands by fusion with streptavidin or streptavidin variants.

The comparison of small and large GNR OCT signals empirically demonstrates a key benefit of larger GNRs for future applications in biomedical imaging. Consistent with theory and simulation, large GNRs scatter significantly more light than small GNRs, making them ideal agents for scattering-based imaging modalities including OCT and Surface Enhanced Raman Scattering (SERS). Because the total interaction with light is greater for large GNRs than commonly-used small GNRs, large GNRs may also be used in a variety of near-infrared imaging techniques including photoacoustics and two-photon luminescence to improve sensitivity and thus enhance molecular contrast.

In summary, this study provides fundamental insights into the mechanisms through which colloidal stability is achieved for particles of different sizes. Large GNRs are not stabilized by the steric effects through which PEG chains improve the stability of smaller GNRs. Unlike small GNRs, large GNRs may require stabilization through stronger electrostatic repulsive interactions among particles. This work has also demonstrated the practical benefits of understanding large GNR stability. From an applications-based standpoint, large GNRs (and perhaps unique nanoparticles in general) should be functionalized using tailored surface chemistry methods if their advantages in biomedical imaging and therapy are to be realized. In achieving one such tailored approach, disclosed herein is an improved nanoparticle that can immediately benefit a plethora of current contrast-enhanced imaging techniques.

Materials And Methods

GNRs within two different size regimes were synthesized using modified versions of two previously reported seed-mediated growth methods. Small GNRs (~50×15 nm) were prepared according to an original method by Nikoobakht and El-Sayed. Briefly, a seed solution was prepared by adding 5 mL 0.2 M of CTAB (≥98%, TCI, CAS#57-09-0) and 5 mL of 0.0005 M $HAuCl_4$ (≥49.0% Au basis, Sigma-Aldrich, CAS#16961-25-4) with gentle stirring, after which 0.6 mL of 0.01 M $NaBH_4$ (≥99%, Fluka, CAS#16940-66-2) was added. This solution was stirred for 2 min at 25° C. prior to use. Two growth solutions (Small GNRs I and II) were prepared by adding 5 mL of 0.2 M CTAB to 2254 (I) or 2754 (II) of 0.004 M $AgNO_3$ (99.9999% trace metal basis, Aldrich, CAS#7761-88-8) at 25° C. under gentle stirring. 5 mL of 0.001 M $HAuCl_4$ was then added to each growth solution and mixed. Then, 70 µL of 0.0788 M L-Ascorbic Acid (reagent grade, Sigma, CAS#50-81-7) was mixed into each solution. Finally, 12 µL of the seed solution was stirred into each growth solution and the solutions were left undisturbed at 30° C. for 2 hours. Large GNRs (~90×30 nm) were prepared by adapting a two-surfactant method reported by the Murray group at the University of Pennsylvania. 9.0 g CTAB and 1.234 g sodium oleate (NaOL, ≥97%, TCI, CAS#143-19-1) were added to 250 mL of $H_2O$ at 50° C. and stirred until dissolved. The temperature was then decreased to 30° C. Once this solution reached 30° C., either 25 mL (Large GNRs I) or 50 mL (Large GNRs II) of 0.004 M $AgNO_3$ was added. Each solution was left undisturbed for 15 min, after which 250 mL of 0.00086 M $HAuCl_4$ was added to each and stirred for 90 min at 700 rpm. During this time, the yellow-gold solution growth solutions turned colorless. A seed solution was also prepared during this time by adding 5 mL 0.2 M CTAB, 5 mL 0.000043 M $HAuCl_4$, and 0.6 mL of 0.01 M $NaBH_4 \pm 0.4$ mL $H_2O$. This seed solution was aged for 30 minutes prior to use. 90 minutes after the addition of $HAuCl_4$ to the growth solutions, 2.1 mL of 12.1 N hydrochloric acid (HCl, Fisher, CAS#7647-01-0) was added to each growth solution and stirred at 400 rpm for 15 min. 1.25 mL of 0.064 M ascorbic acid was added to each growth and stirred vigorously (1200 rpm) for 30 seconds. Finally, 0.1 mL of aged seed solution was added to each growth (also at 1200 rpm stirring), and each growth solution was left undisturbed without stirring for 12 hours at 30° C. Four different batches of GNRs (Small GNRs 1, Small GNRs 11, Large GNRs 1, and Large GNRs II) were made using the protocols described above. While the protocols produce particles within distinct size regimes, Small GNRs I and Large GNRs I both exhibited ~750 nm longitudinal surface plasmon resonance (LSPR) while Small GNRs II and Large GNRs II exhibited ~800 nm LSPR, facilitating spectral and stability comparisons between particles.

Each of the four GNR batches was prepared with three different surface coatings: CTAB, mPEG$_{5000}$-SH (MW ~5000 Da, Laysan Bio, Arab, Ala.), or Poly(sodium 4-styrenesulfonate) (PSS, MW ~70 kDa, Aldrich, CAS#25704-18-1). GNRs-CTAB were taken directly from as-synthesized growth solutions. GNRs-mPEG were prepared using a modified version of a previous protocol[6] by incubating as-synthesized GNRs-CTAB solutions with 1 mg/mL mPEG$_{5000}$-SH for 24 hrs at room temperature with gentle mixing. GNRs-PSS (Large GNRs only) were prepared using a modified method[7] by adding 0.1 mL of 0.001 M PSS to 1 mL of GNRs-CTAB. Both GNRs-mPEG and GNRs-PSS were washed once by centrifugation (2550×g for 10 min at 25° C. in an Eppendorf 5417R microcentrifuge) to remove excess CTAB. Because this step was required to remove excess CTAB, measurements of mPEG$_{5000}$-SH or PSS particles start at 1× wash rather than the 0× wash step at which CTAB GNR measurements start. This step was taken to maintain the integrity of comparisons of particle stability with respect to surface coating and rounds of washing.

The four batches of unwashed GNRs-CTAB were initially characterized in terms of spectral characteristics, physical size, and surface potential. Spectra were measured using a Cary 6000i spectrophotometer. All GNR batches were adjusted to the same optical density (OD) prior to characterization for comparison. Size distributions and average dimensions for each GNR batch were determined from images taken by a JEOL TEM 1400 electron microscope. Zeta potential for each batch was measured using a Malvern Zetasizer Nano ZS. In addition to this initial characterization, spectra and zeta potential for each GNR batch with each surface coating were measured after each of four wash steps to characterize particle stability in distilled deionized (DDI) H$_2$O. A single wash step consisted of the following: centrifugation of 1 mL GNR solution (2550×g for 10 min at 25° C.), removal of 950 μL supernatant, and resuspension of the GNR pellet with 950 μL fresh DDI H$_2$O. Thus, one wash resulted in a ~20-fold decrease in concentration of any small molecules in the supernatant.

In addition to the experiments described above, the stability of select GNRs in biological serum was tested. Large GNRs coated with either mPEG$_{5000}$-SH (Large GNRs-mPEG) or PSS (Large GNRs-PSS) were incubated for 3 hrs with Fetal Bovine Serum (FBS) at room temperature. GNR solutions were then centrifuged and washed 3× to remove excess FBS. GNRs were characterized by absorbance spectra after each wash to assess serum stability.

To demonstrate their utility for targeted biological studies, it was tested whether GNRs-PSS could be conjugated to retain binding capacity for specific ligands. An independently-prepared batch of Large GNRs-PSS (897 nm LSPR) at OD 20 was incubated with 1 mg/mL Biotin-PEG$_{5000}$-SH (MW ~5000 Da, NanoCS) for 24 hrs at room temperature (Large GNRs-PSS-PEG-Biotin). Large GNRs-PSS-PEG-Biotin were washed 2× to remove excess reagents from the supernatant. Large GNRs-PSS-mPEG were also prepared using the same approach. After preparation, 100 μL of each particle type was incubated with 10 μL of streptavidin-coated polystyrene beads (3 μm avg. diameter, 0.5% w/v, Spherotech, product #SVP-30-5) for 1 hr with 1500 rpm vortexing using a Multitherm tabletop shaker (Benchmark, Edison, N.J.). After the incubation, each GNR+bead solution was diluted to a total volume of 1 mL. Each solution was centrifuged for 20 sec at 1000×g. This time and speed are insufficient to pellet free GNRs, but the majority of beads and any associated particles do pellet under this condition. Because of the high affinity of the interaction between biotin and streptavidin, this method enabled us to determine whether Large GNRs-PSS-PEG-Biotin were capable of specific binding to a streptavidin substrate. Photographs were taken of bead pellets and supernatant to qualitatively assess the presence of GNR binding for each condition. Vis-NIR spectra were also taken of each supernatant to indirectly quantify GNR binding to pelleted streptavidin-coated beads. A blocking assay to test the molecular nature of GNR binding was also performed by incubating the streptavidin beads with an excess (1 mg/mL) of free biotin (≥99%, Sigma-Aldrich, CAS: 58-85-5) prior to the addition of GNRs. This experiment was repeated with streptavidin beads in the presence of FBS during GNR incubation to assay whether specific GNR binding can occur in the presence of non-specific proteins.

Solutions of small and large GNRs (each from batch II) were prepared at 1) optical density (OD) 1 with respect to 800 nm and 2) 2×10$^{10}$ nps/mL (equal to OD 1 for large GNRs and OD 0.125 for small GNRs). Each GNR solution was added to a glass capillary tube with an inner diameter of 400 μm. Pairs of tubes containing equal OD or equal number of GNRs were then imaged with a Ganymede SD-OCT system (ThorLabs, Newton, N.J.). The OCT light source is a superluminescent diode (SLD) operating at 30 kHz and centered at 900 nm with a 200 nm full bandwidth. The system has 2 μm lateral and 3 μm axial resolution. OCT images of GNRs were produced by averaging 100 frames acquired B-scan mode. After acquisition, fields of view (each 15,000 pixels) at the same focal depth within each sample tube were used to calculate mean OCT signal+/− standard deviation. Another field of view at the focal depth was acquired to quantify the system noise level. The mean noise level was subtracted from the mean signal of each GNR solution to quantify relative OCT contrast for each particle. Subsets (600 pixels each) of each original FOV were used in two-tailed student's t-tests to compare the average signal from OD 1 large GNRs versus OD 1 small GNRs and 2×10$^{10}$ nps/mL large GNRs versus 2×10$^{10}$ nps/mL small GNRs.

What is claimed is:

1. A composition comprising:
   a plurality of gold nanorods within an aqueous solution, the plurality of gold nanorods prepared for in vivo optical coherence tomography imaging of a target tissue,
   each of the plurality of gold nanorods having at least one surface,
   the plurality of gold nanorods having an average length of between about 90 nm and about 150 nm and an average width of between about 25 nm and about 50 nm,
   each of the plurality of gold nanorods being coated with polystyrene sulfonate (PSS),
   the polystyrene sulfonate coating configured to maintain nonaggregation of the plurality of gold nanorods during the in vivo optical coherence tomography imaging of the target tissue.

2. The composition of claim 1, wherein the average length is about 90 nm and the average width is about 30 nm.

3. The composition of claim 1, wherein the plurality of gold nanorods is within the aqueous solution as a colloidal suspension.

4. The composition of claim 1, wherein the PSS is electrostatically adsorbed on the at least one surface of the plurality of gold nanorods.

5. The composition of claim 4, further comprising:
one or more functional groups associated with the PSS.

6. The composition of claim 5, wherein the one or more functional groups are covalently associated with the PSS.

7. The composition of claim 5, wherein the one or more functional groups are electrostatically associated with the PSS.

8. The composition of claim 5, wherein the one or more functional groups are associated with the PSS via one or more thiol groups.

9. The composition of claim 5, wherein the one or more functional group includes a biotin.

10. The composition of any one of claim 5, wherein the one or more functional groups includes any of an avidin, a poly(ethylene) glycol (PEG), an antibody, or an antigen binding portion of the antibody.

11. The composition of claim 9, wherein the biotin is PEGylated biotin.

12. The composition of claim 5, wherein the one or more functional group comprises a biotinylated ligand.

13. The composition of claim 12, wherein the biotinylated ligand is at least one of a biotinylated antibody, a fragment of the biotinylated antibody, a biotinylated antibody-drug conjugate, a biotinylated peptide, a biotinylated enzyme, a biotinylated G protein coupled receptor (GPCR) ligand, or a biotinylated transmembrane receptor ligand.

14. The composition of claim 4, further comprising:
a plurality of polystyrene beads conjugated to at least a portion of the plurality of gold nanorods.

15. A method of imaging of a target tissue, comprising:
administering, to the target tissue, a composition including a plurality of gold nanorods each having at least one surface, at least one of the gold nanorods of the plurality of gold nanorods including an anionic polymer electrostatically adsorbed on the at least one surface of the gold nanorod, the anionic polymer being polystyrene sulfonate (PSS), the plurality of gold nanorods having an average length of between about 90 nm and about 150 nm and an average width of between about 25 nm and about 50 nm;
imaging, via optical coherence tomography imaging, the target tissue using an imaging apparatus to acquire an interference spectrum;
generating, based on the interference spectrum, a first spectral band and a second spectral band, the second spectral band different from the first spectral band;
generating a first image based on the first spectral band;
generating a second image based on the second spectral band;
generating difference information by subtracting one of the first image and the second image from the other of the first image and the second image; and
transmitting an indication of the difference information.

16. The method of claim 15, wherein the plurality of gold nanorods is present as a colloidal suspension.

17. A composition comprising:
a plurality of gold nanorods each having at least one surface, at least one of the gold nanorods of the plurality of gold nanorods including polystyrene sulfonate (PSS) electrostatically adsorbed on the at least one surface of the gold nanorod, the plurality of gold nanorods prepared for in vivo imaging of a target tissue,
the plurality of gold nanorods having an average length of between about 90 nm and about 150 nm and an average width of between about 25 nm and about 50 nm,
the polystyrene sulfonate (PSS) coating configured to maintain nonaggregation of the plurality of gold nanorods during the in vivo imaging of the target tissue to maintain an enhanced optical performance produced by the length and width of the plurality of gold nanorods.

18. The composition of claim 1, wherein an average aspect ratio of the plurality of gold nanorods is about 3.

19. The method of claim 15, wherein a majority of the plurality of gold nanorods include the anionic polymer electrostatically adsorbed on the at least one surface, the majority of the plurality of gold nanorods including one or more functional groups associated with the anionic polymer.

20. The method of claim 19, wherein the one or more functional group includes any of a biotin, an avidin, a poly(ethylene) glycol (PEG), an antibody, or an antigen binding portion of the antibody.

21. The composition of claim 17, wherein an average aspect ratio of the plurality of gold nanorods is about 3.

22. The composition of claim 17, wherein a majority of the plurality of gold nanorods include the PSS electrostatically adsorbed on the at least one surface, the majority of the plurality of gold nanorods including one or more functional groups associated with the PSS.

23. The composition of claim 22, wherein the one or more functional group includes any of a biotin, an avidin, a poly(ethylene) glycol (PEG), an antibody, or an antigen binding portion of the antibody.

* * * * *